United States Patent
Kwon et al.

(10) Patent No.: US 9,566,709 B2
(45) Date of Patent: Feb. 14, 2017

(54) ROBOTS COMPRISING MULTI-TOOL MODULES HAVING REDUNDANCY AND METHODS OF CONTROLLING THE SAME

(71) Applicant: Samsung Electronics Co., Ltd., Suwon-Si, Gyeonggi-Do (KR)

(72) Inventors: Woong Kwon, Seongnam-si (KR); Bok Man Lim, Yongin-si (KR); Gurel Ogan, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/217,808

(22) Filed: Mar. 18, 2014

(65) Prior Publication Data
US 2014/0277741 A1 Sep. 18, 2014

(30) Foreign Application Priority Data

Mar. 15, 2013 (KR) .................. 10-2013-0028308

(51) Int. Cl.
*B25J 9/16* (2006.01)
*A61B 34/37* (2016.01)
(Continued)

(52) U.S. Cl.
CPC ............ *B25J 9/1607* (2013.01); *A61B 34/30* (2016.02); *A61B 34/37* (2016.02); *B25J 9/1689* (2013.01);
(Continued)

(58) Field of Classification Search
CPC B25J 9/1607; A61B 19/2203; A61B 19/5212; A61B 2019/2215; A61B 2019/2223; A61B 2019/2276; A61B 2019/5231; A61B 2019/5276; G05B 2219/39079; G05B 2219/40182; G05B 2219/40333; G05B 2219/40336; G05B 2219/40338; G05B 2219/40352; G05B 2219/40371; G05B 2219/35117
See application file for complete search history.

(56) References Cited

U.S. PATENT DOCUMENTS

| 5,294,873 | A | * | 3/1994 | Seraji | ................. B25J 9/1638 318/561 |
|---|---|---|---|---|---|
| 5,430,643 | A | * | 7/1995 | Seraji | ................. B25J 9/1643 318/568.11 |
| 8,029,516 | B2 | | 10/2011 | Mohr et al. | |
| 2007/0013336 | A1 | * | 1/2007 | Nowlin et al. | ........... 318/568.21 |
| 2007/0162164 | A1 | | 7/2007 | Dariush | |
| 2007/0283970 | A1 | * | 12/2007 | Mohr et al. | .................. 128/898 |
| 2007/0287889 | A1 | | 12/2007 | Mohr | |
| 2008/0065103 | A1 | | 3/2008 | Cooper et al. | |
| 2009/0326552 | A1 | * | 12/2009 | Diolaiti | ....................... 606/130 |
| 2010/0274087 | A1 | | 10/2010 | Diolaiti et al. | |
| 2010/0332033 | A1 | * | 12/2010 | Diolaiti et al. | ............... 700/259 |

(Continued)

FOREIGN PATENT DOCUMENTS

KR 20110120476 A 11/2011

OTHER PUBLICATIONS

Choi, K., et al., Online Motion Retargetting, J. Visual. Comput. Animat. 2000; 11: 223-235 (2000).

(Continued)

*Primary Examiner* — Abby Lin
(74) *Attorney, Agent, or Firm* — Harness, Dickey & Pierce, P.L.C.

(57) ABSTRACT

A robot may include: a multi-tool module having redundancy, the multi-tool module including a guide tube and a plurality of tools configured to operate while interacting with the guide tube and extended from the guide tube; and/or a controller configured to generate a control signal regarding motion of the multi-tool module in a joint space based on motion instruction information regarding distal ends of the plurality of tools in a task space. The redundancy may reflect that a number of degrees of freedom of the multi-tool module in the joint space is greater than a number of degrees of freedom of the task space. The control signal may be generated using the redundancy.

13 Claims, 19 Drawing Sheets

(51) Int. Cl.
*A61B 34/30* (2016.01)
*A61B 90/00* (2016.01)
*A61B 17/00* (2006.01)

(52) U.S. Cl.
CPC .... *A61B 90/361* (2016.02); *A61B 2017/00225* (2013.01); *A61B 2034/302* (2016.02); *A61B 2034/742* (2016.02); *A61B 2090/373* (2016.02); *A61B 2090/378* (2016.02); *G05B 2219/39079* (2013.01); *G05B 2219/40182* (2013.01); *G05B 2219/40333* (2013.01); *G05B 2219/40336* (2013.01); *G05B 2219/40338* (2013.01); *G05B 2219/40352* (2013.01); *G05B 2219/40371* (2013.01); *G05B 2219/45117* (2013.01)

(56) References Cited

U.S. PATENT DOCUMENTS

2011/0230894 A1  9/2011  Simaan et al.
2012/0004775 A1* 1/2012  Andoh .......................... 700/259

OTHER PUBLICATIONS

Mar. 20, 2015, Extended European Search Report issued in corresponding European Application No. 14160269.8.

* cited by examiner

FIG.1
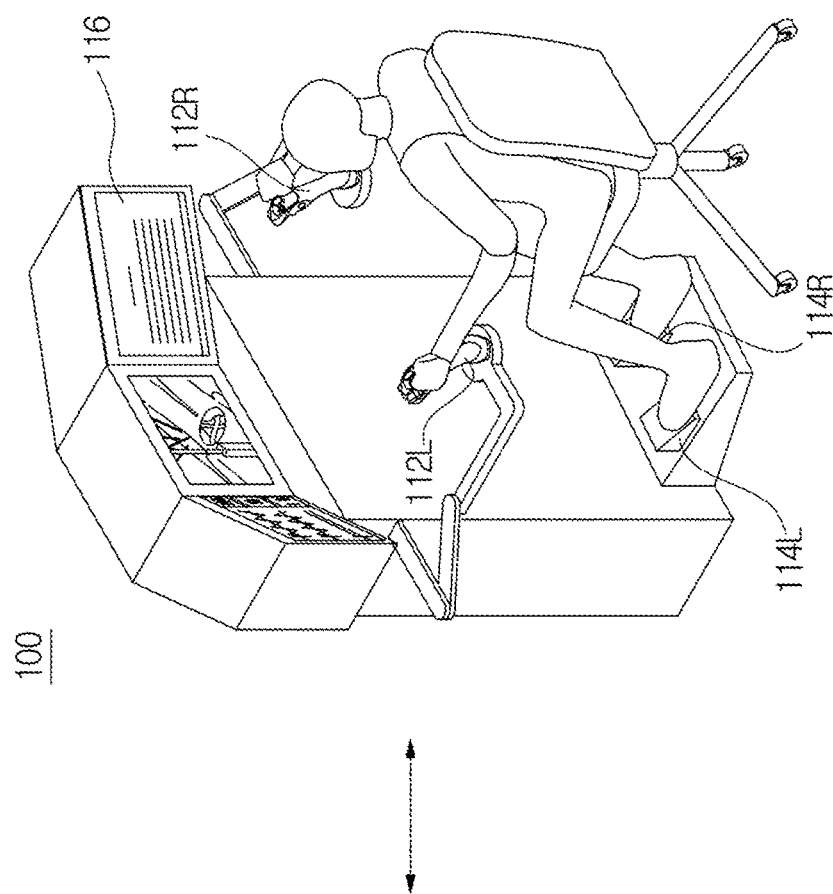
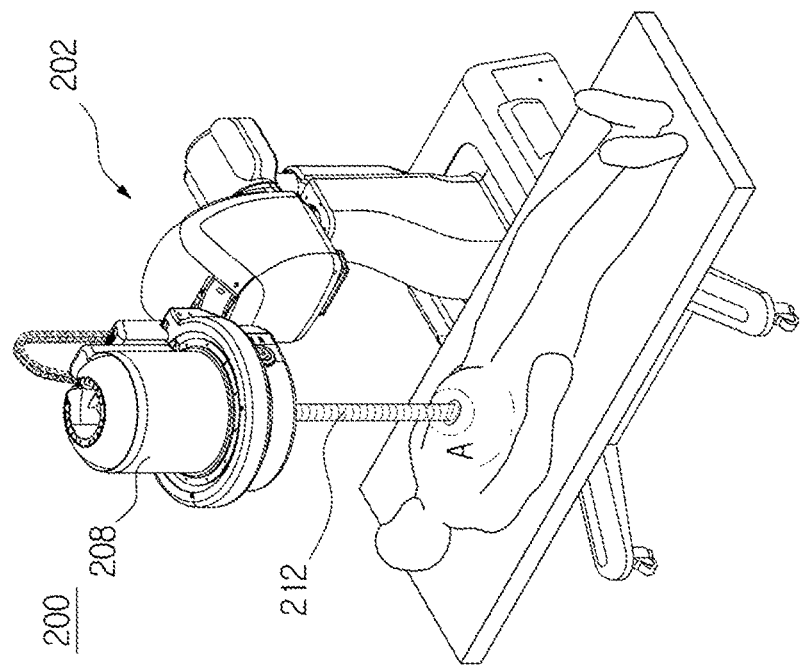

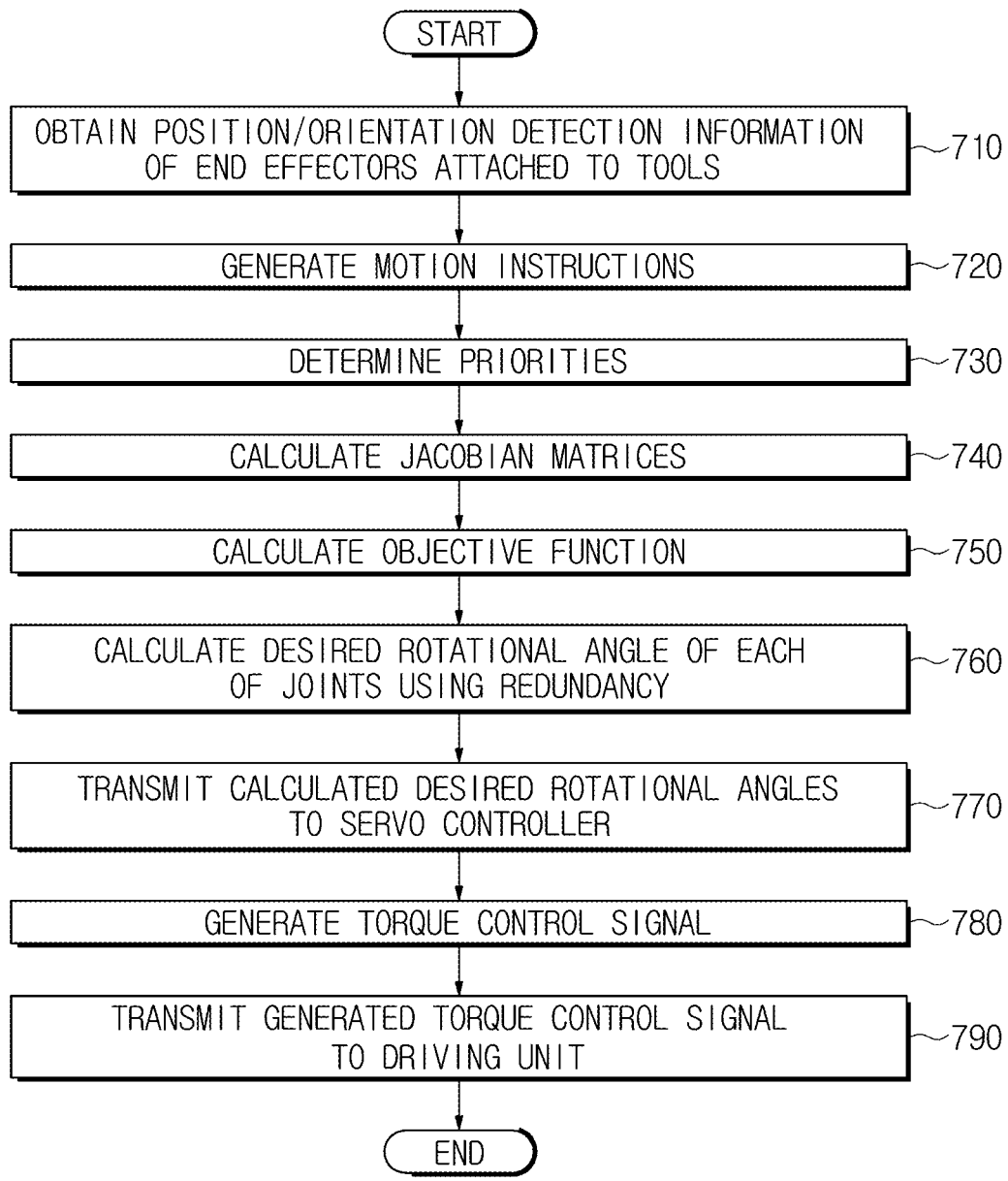

ROBOTS COMPRISING MULTI-TOOL MODULES HAVING REDUNDANCY AND METHODS OF CONTROLLING THE SAME

CROSS-REFERENCE TO RELATED APPLICATION(S)

This application claims priority from Korean Patent Application No. 10-2013-0028308, filed on Mar. 15, 2013, in the Korean Intellectual Property Office (KIPO), the entire contents of which are incorporated herein by reference.

BACKGROUND

1. Field

Some example embodiments may relate to robots configured to employ a plurality of tools and/or methods of controlling the same.

2. Description of Related Art

In general, a mechanical apparatus that makes a movement similar to a human motion using an electrical or magnetic action may be referred to as a robot. Robots, such as surgical robots, housekeeper robots, service robots for public places, aerospace remote robots, and dangerous substance handling robots, recently may be used in various fields owing to development of control technology. These robots may perform tasks using a manipulator configured to make a movement closer to an arm or hand's motion based on electrical and/or mechanical mechanisms.

A surgical robot, among various types of robots described above, may include a master device that generates and transmits necessary signals due to a manipulator's (typically a doctor) manipulation and a slave robot that performs manipulations required for surgery on patients in response to signals received from the master device, even though the slave robot may be located far from the master device. In this regard, the master device may perform remote control of operations of the slave robot based on various physical information such as force, position, tactility, temperature, humidity, illuminance, and the like that may be detected by the slave robot.

In general, the slave robot may be installed in an operating room, the master device may be installed in a manipulation room, and the master device and the slave robot may be connected to each other via wired or wireless communication to perform surgery at a distance. The doctor may be in the same room, in a different room, or in a different facility (perhaps located in another country).

Surgical robot systems may provide numerous other advantages, such as potentially improved precision, better ability to monitor the patient, and ability to record the surgical procedure for training, qualification, and evidentiary purposes.

Minimally invasive surgery using an existing surgical robot may be based mainly on multi-port surgery, whereby a plurality of surgical instruments each having a distal end to which an end effector may be attached, may be put into a patient's body through a plurality of incision holes. However, an example of single-port surgery, whereby the plurality of surgical instruments may be put into the patient's body through one incision hole, is recently increasing. Single-port surgery may be several advantages, such as a shorter healing period than in the multi-port surgery and/or less surgical trace than in the multi-port surgery in terms of appearance. However, in the single-port surgery, there may be a possibility that interference between the surgical instruments could occur, and the range of applicable surgeries may be limited due to limitations in workspaces of the surgical instruments.

Although some example embodiments will be described with relation to surgical robots and methods of controlling those robots, those skilled in the art will appreciate that some example embodiments may be applied to other types robots, such as robots not used in the medical field (e.g., aerospace robots, robots for handling hazardous materials, patrol robots, military robots), humanoid robots, or more general purpose systems and/or methods of controlling such systems.

SUMMARY

Some example embodiments may provide robots configured to employ a plurality of tools.

Some example embodiments may provide methods for controlling robots configured to employ a plurality of tools.

In some example embodiments, a robot may comprise: a multi-tool module having redundancy, the multi-tool module comprising a guide tube and a plurality of tools configured to operate while interacting with the guide tube and extended from the guide tube; and/or a controller configured to generate a control signal regarding motion of the multi-tool module in a joint space based on motion instruction information regarding distal ends of the plurality of tools in a task space. The redundancy may reflect that a number of degrees of freedom of the multi-tool module in the joint space is greater than a number of degrees of freedom of the task space. The control signal may be generated using the redundancy.

In some example embodiments, each of the guide tube and the plurality of tools may comprise a plurality of links and a plurality of joints. The distal ends of the plurality of tools may comprise end effectors.

In some example embodiments, the controller may be configured to calculate a Jacobian matrix corresponding to the motion instruction information, and/or may be configured to generate the control signal based on the motion instruction information and the calculated Jacobian matrix using the redundancy.

In some example embodiments, the controller may be configured to calculate an objective function of the robot when the control signal is generated. The objective function may represent a weighted sum of a plurality of individual objective functions.

In some example embodiments, each of the plurality of individual objective functions may comprise a reciprocal number of a distance between each of the tools and a joint limit.

In some example embodiments, each of the plurality of individual objective functions may comprise a reciprocal number of a distance between each of the tools and a singular pose.

In some example embodiments, each of the plurality of individual objective functions may comprise a joint torque square sum.

In some example embodiments, each of the plurality of individual objective functions may comprise a reciprocal number of a distance between each of the tools and a peripheral obstacle.

In some example embodiments, the controller may be configured to generate the control signal in which the calculated objective function of the robot is optimized or sub-optimized.

In some example embodiments, the robot may further comprise: a storage unit. The storage unit may be configured to store an algorithm required to calculate the Jacobian matrix and information regarding a kinematics structure of the robot, the plurality of individual objective functions for achieving a plurality of individual objectives required to calculate the objective function, and weights multiplied with the plurality of individual objective functions depending on a type of a task performed by the robot.

In some example embodiments, when priorities are set to the motion instruction information regarding the distal ends of the plurality of tools in the task space, the controller may be configured to calculate Jacobian matrices corresponding to the motion instruction information having a relatively high priority in the task space and the motion instruction information having a relatively low priority in the task space, and is configured to generate the control signal based on the motion instruction information in the task space to which the priorities are set and the calculated Jacobian matrices using the redundancy.

In some example embodiments, the controller may be configured to calculate an objective function of the robot when the control signal is generated. The objective function may represent a weighted sum of a plurality of individual objective functions.

In some example embodiments, the controller may be configured to generate the control signal in which the calculated objective function of the robot is optimized or sub-optimized.

In some example embodiments, the robot may further comprise: a storage unit. The storage unit may be configured to store the priorities set to the motion instruction information regarding the distal ends of the plurality of tools in the task space, an algorithm required to calculate the Jacobian matrices and information regarding a kinematics structure of the robot, the plurality of individual objective functions for achieving a plurality of individual objectives required to calculate the objective function, and weights multiplied with the plurality of individual objective functions depending on a type of a task performed by the robot.

In some example embodiments, a method of controlling a robot that comprises a multi-tool module, having redundancy, comprising a guide tube and a plurality of tools configured to operate while interacting with the guide tube and extended from the guide tube, may comprise: generating motion instruction information regarding distal ends of the plurality of tools in a task space; and/or generating a control signal regarding motion of the multi-tool module in a joint space based on the generated motion instruction information in the task space. The redundancy may reflect that a number of degrees of freedom of the multi-tool module in the joint space is greater than a number of degrees of freedom of the task space. The control signal may be generated using the redundancy.

In some example embodiments, each of the guide tube and the plurality of tools may comprise a plurality of links and a plurality of joints. The distal ends of the plurality of tools may comprise end effectors.

In some example embodiments, the generating of the control signal may comprise: calculating a Jacobian matrix corresponding to the motion instruction information; and/or generating the control signal based on the motion instruction information and the calculated Jacobian matrix using the redundancy.

In some example embodiments, the generating of the control signal may comprise: calculating an objective function of the robot; and/or generating the control signal in which the calculated objective function of the robot is optimized or sub-optimized.

BRIEF DESCRIPTION OF THE DRAWINGS

The above and/or other aspects and advantages will become more apparent and more readily appreciated from the following detailed description of example embodiments, taken in conjunction with the accompanying drawings, in which:

FIG. 1 is a perspective view illustrating an entire structure of a surgical robot in accordance with some example embodiments;

FIG. 17 is a flowchart illustrating a method of controlling a humanoid robot in accordance with some example embodiments.

DETAILED DESCRIPTION

Figure 2:
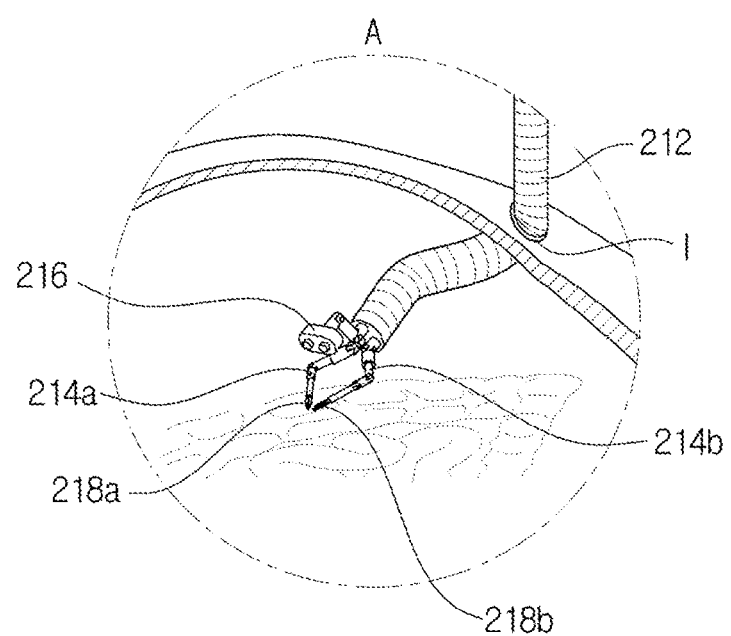
FIG. 2 illustrates an inside of a portion illustrated in FIG. 1.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

FIG. 1 is a perspective view of an entire structure of a surgical robot in accordance with some example embodiments, and FIG. 2 illustrates an internal structure of a portion A illustrated in FIG. 1. In particular, FIG. 1 illustrates a single-port robot in which a plurality of surgical instruments each having an end to which surgical tools are attached, is put into a patient's body through one incision hole so that surgery can be performed in various parts of the human body. The following requirements that will be described below are necessary in surgery using a single-port surgical robot. Firstly, since the plurality of surgical instruments are put into the body through one incision hole and then need to be moved to an arbitrary position for a surgery task, a workspace of the surgical instruments is required to be wide. Secondly, the surgical instruments need to have a high degree of freedom so that they can perform various tasks and collision with a body tissue, such as an abdominal cavity wall, can be minimized. Thirdly, when the surgical instruments are put into the body, they are required to be flexible and to have high rigidity when they perform a surgical task. That is, when surgery using a single-port surgical robot is performed, surgical instruments that simultaneously satisfy a wide workspace in which the surgical instruments are capable of moving freely, a high degree of freedom, high rigidity and flexibility, need to be guaranteed.

In some example embodiments, a degree of freedom (DOF) is a degree of freedom in forward kinematics or inverse kinematics. The DOF of kinematics is the number of independent motions of a mechanism, or the number of variables for determining independent motions at relative positions between links. For example, an object in a three-dimensional space including the x-axis, the y-axis, and the z-axis has at least one of three degrees of freedom (3 DOF)(position at each axis) for determining a spatial position of the object and three degrees of freedom (3 DOF) (rotational angle with respect to each axis) for determining a spatial orientation of the object. If the object is movable along each axis and is rotatable around each axis, the object may have six degrees of freedom (6 DOF).

As illustrated in FIG. 1, the surgical robot includes a slave robot 200 that performs surgery on a patient that lies on an operating table and a master device 100 that remotely controls the slave robot 200 through a manipulator's (typically a surgeon) manipulation. The master device 100 generates a control signal according to the manipulator's (typically a surgeon) manipulation and transmits the generated control signal to the slave robot 200. Meanwhile, the slave robot 200 receives the control signal from the master device 100 and moves according to the received control signal so as to perform a manipulation required for surgery on the patient. In some example embodiments, the master device 100 and the slave robot 200 are not necessarily separated from each other as physically independent, separate devices but may be integrated with each other and may be configured as one body shape.

In some example embodiments, the master device 100 may not be a single robot, but may include more than one robot, each performing one or more functions of the master device 100. Thus, in some example embodiments, the functionality of the master device 100 may be distributed.

Similarly, in some example embodiments, the slave robot 200 may not be a single robot, but may include more than one robot, each performing one or more functions of the slave robot 200. Thus, in some example embodiments, the functionality of the slave robot 200 may be distributed.

Therefore, in some example embodiments, the functionality of the master device 100, the slave robot 200, or the master device 100 and the slave robot 200 may be distributed.

In some example embodiments, the master device 100 may be required to perform certain functions, but may or may not perform other functions while maintaining its role as the master device 100. One or more of these other functions may be shared with or performed by the slave robot 200 (which maintains its role as the slave robot 200). Similarly, in some example embodiments, the slave robot 200 may be required to perform certain functions, but may or may not perform other functions while maintaining its role as the slave robot 200. One or more of those other functions may be shared with or performed by the master device 100 (which maintains its role as the master device 100).

Therefore, in some example embodiments, the required functionality of the master device 100 and the slave robot 200 may be maintained, while functionality that may be shared with or performed by the other robot may be so shared with or performed by the other robot consistent with the master device 100 maintaining its role as the master device 100 and the slave robot 200 maintaining its role as the slave robot 200.

As illustrated in FIG. 1, the slave robot 200 may include a mounting arm 202 and a cylindrical casing 208.

The mounting arm 202 of the slave robot 200 may be implemented to be driven with multiple degrees of freedom. The mounting arm 202 includes a plurality of links (see 206a, 206b, and 206c of FIG. 3A) and a plurality of joints (see 204a, 204b, and 204c of FIG. 3A).

Also, the casing 208 is connected to an upper part of the mounting arm 202. A guide tube 212 including a plurality of tools 214a and 214b and/or an endoscope 216, and a driving unit (see 270 of FIG. 3B) for driving the plurality of tools 214a and 214b and/or the endoscope 216 and the guide tube 212 may be installed in the casing 208. In some example embodiments, the guide tube 212 is connected to and installed at the mounting arm 202. When the slave robot 200 does not perform surgery, the guide tube 212 is embedded in the casing 208, and when the slave robot 200 performs surgery, the guide tube 212 embedded in the casing 208 goes out of the casing 208 and is inserted into a patient's body, as illustrated in FIGS. 1 and 2. A case that the guide tube 212 is inserted into the patient's body and performs a surgical task, i.e., an internal shape of a portion A illustrated in FIG. 1 will be described below in more detail. As illustrated in FIG. 2, if the guide tube 212 is put into the body through an incision hole I formed in the patient's skin and then is close to a part on which an operation is to be performed (an operating part), the plurality of tools 214a and 214b and the endoscope 216 extend from the guide tube 212 so that the surgical task can be performed. In some example embodiments, the guide tube 212, the plurality of tools 214a and 214b, and the endoscope 216 may include a plurality of links and a plurality of joints and may be implemented to be driven with multiple degrees of freedom, like in the mounting arm 202. Surgical tools that perform a direct surgical task for contacting an organ, cutting and suturing within an abdominal cavity, such as forceps, jaw, grasper, scissors, stapler, cautery, and needle, i.e., end effectors 218a and 218b are mounted in each distal end of the plurality of tools 214a and 214b.

Although the endoscope 216 may be one of the plurality of tools 214a and 214b that extend from the guide tube 212 in a broad meaning, in consideration of characteristics of the surgical robot, the plurality of tools 214a and 214b each having a distal end in which the end effectors 218a and 218b that perform direct surgical operations, such as cutting and suturing, on the operating part are disposed, and the endoscope 216 having multiple joints for assisting with operations of the end effectors 218a and 218b without performing direct operations on the operating part will be separately described below.

In some example embodiments, various surgical endoscopes, such as a thoracoscope, an arthroscope, and a rhinoscope, as well as a laparoscope that is mainly used in robot surgery, may be used as the endoscope 216.

The master device 100 may include master manipulation units 112L and 112R, clutch pedal sensors 114L and 114R, and a display unit 116. Master manipulation units 112L and 112R may facilitate surgical procedures by more than one doctor simultaneously.

The master device 100 includes the master manipulation units 112L and 112R that the manipulator grasps with his/her hands and manipulates. The manipulator manipulates positions and functions of the mounting arm 202, the guide tube 212, the plurality of tools 214a and 214b, and the endoscope 216 through the master manipulation units 112L and 112R. The master manipulation units 112L and 112R may be implemented with 6 degrees of freedom so as to control translational motions of the mounting arm 202 in an x-axis, a y-axis, and a z-axis in a three-dimensional (3D) space and rotational motions in a roll direction, a pitch direction, and a yaw direction. The master manipulation units 112L and 112R may be implemented with two handles, as illustrated in FIG. 1, and the control signal generated by the manipulator's handle manipulation is transmitted to the slave robot 200 so that an operation of the slave robot 200 including the mounting arm 202 is controlled. Through the manipulator's handle manipulation, translational motions and rotational motions of the mounting arm 202, the guide tube 212, the plurality of tools 214a and 214b, and the endoscope 216, and substantial surgical tasks (for example, suturing, cannulation, and the like) can be performed.

Also, the master device 100 includes two pedal sensors 114L and 114R on which the manipulator steps or presses with his/her feet, so as to extend a manipulation function of the master manipulation units 112L and 112R.

As an specific example of a method of controlling the operation of the mounting arm 202 using the master manipulation units 112L and 112R including two handles and two pedal sensors 114L and 114R illustrated in FIG. 1, first, position and operation of the mounting arm 202 may be controlled using a left handle 112L, and position and operation of the guide tube 212 may be controlled using a right handle 112R. Also, in a state in which a mode switch (not shown) or a button (not shown) disposed on the master device 100 is manipulated, position and operation of a first tool 214a may be controlled using the left handle 112L, and position and operation of a second tool 214*b* may be controlled using the right handle 112R. In addition (after the mode switch or button is manipulated), in a state in which the left pedal sensor 114L is manipulated, position and operation of the endoscope 216 may be controlled using the left handle 112L. Also, after the mode switch or button is manipulated, in a state in which the right pedal sensor 114R is manipulated, the position and operation of the endoscope 216 may also be controlled using the right handle 112R.

In FIG. 1, two master manipulation units (handles) are mounted on the master device 100. However, a handle may be added so that a plurality of surgical equipment (for example, a guide tube, a plurality of tools) can be manipulated in real-time. In some example embodiments, the handles 112L and 112R may have various mechanical configurations according to their manipulation methods. For example, various input units having a 3D motion, such as a joystick, and operating the mounting arm 202, the guide tube 212, and the plurality of tools 214*a* and 214*b* may be used as the handles 112L and 112R. A plurality of links and a plurality of joints (connection parts between links) are connected to the master manipulation units 112L and 112R. A rotational angle sensor (for example, an encoder) for detecting a rotational angle of each of joints connected to the master manipulation units 112L and 112R may be mounted on each of the plurality of joints connected to the master manipulation units 112L and 112R.

An image input by an endoscope (see 216 of FIG. 2) and/or an ultrasonic probe (not shown) is displayed as a pictorial image on the display unit 116 of the master device 100.

The display unit 116 may include one or more monitors and may cause pieces of information required for surgery to be individually displayed on each monitor. For example, the monitors may support stereoscopic viewing or viewing from multiple angles at the same time. In FIG. 1, the display unit 116 includes three monitors. However, the number of monitors may be determined in various ways according to the type or kind of information to be displayed.

The master device 100 and the slave robot 200 may be coupled to each other via a wired/wireless communication network so that the control signal, an endoscope image input through the endoscope 216, and an ultrasonic image input through the ultrasonic probe (not shown) can be transmitted to the other party (slave robot or master device). If two control signals generated by two master manipulation units (handles) disposed on the master device 100, for example, a control signal for controlling a position of the first tool 214*a* extended from the guide tube 212 and a control signal for controlling a position of the second tool 214*b* extended from the guide tube 212 need to be transmitted at the same time or at approximately the same time, the control signals may be individually transmitted to the slave robot 200.

In some example embodiments, transmitting the control signals "individually" is that one control signal does not affect the other signal without interference. In this way, in order for a plurality of control signals to be individually transmitted, various methods of transmitting the plurality of control signals by adding header information regarding each control signal in an operation of generating the control signals, transmitting the control signals according to their generation order, or transmitting the control signals according to their priorities that are preset regarding their transmission order may be used. In some example embodiments, transmission paths on which the control signals are transmitted, are individually provided so that interference between the control signals can be fundamentally prevented.

Figure 3A:
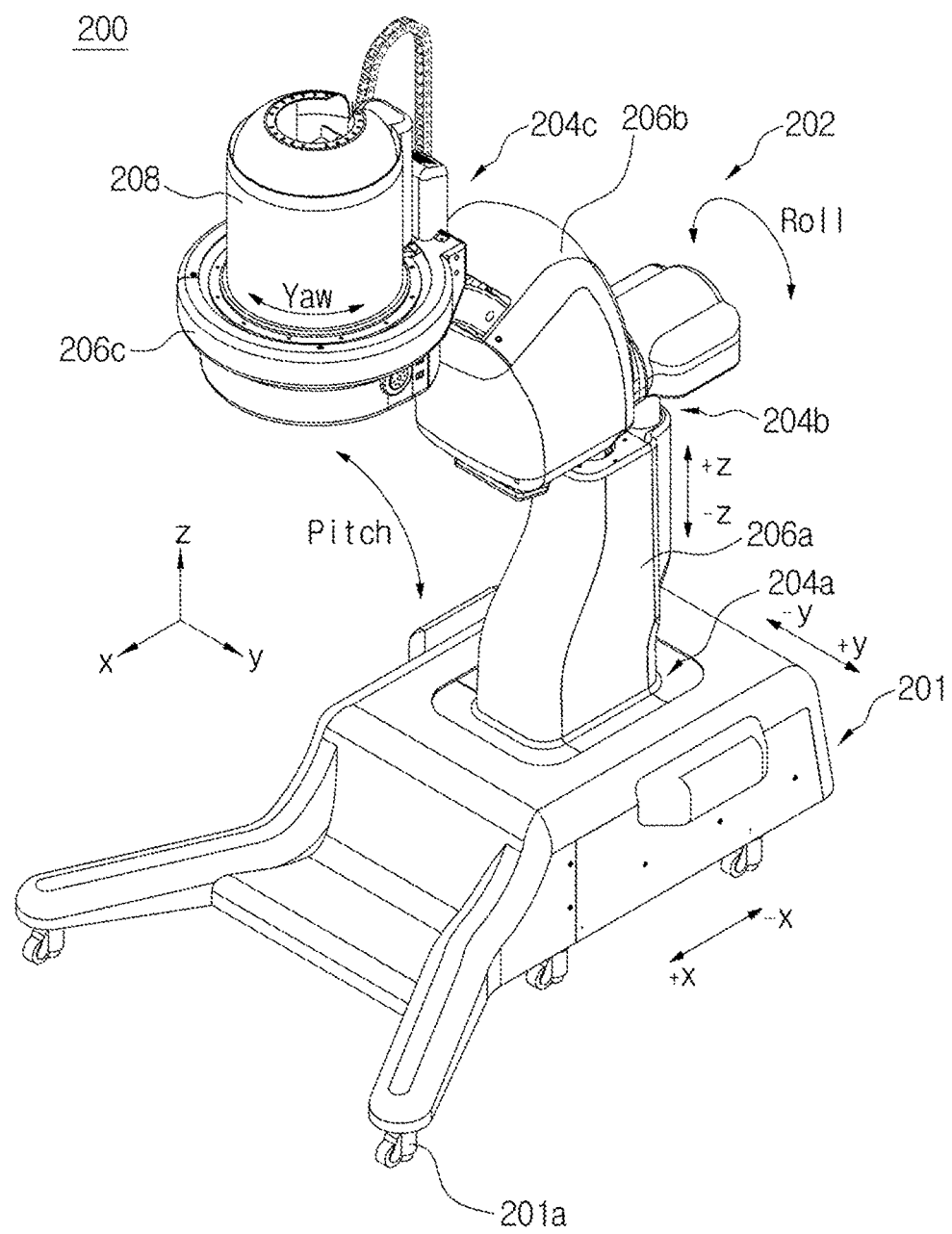
FIG. 3A is a perspective view illustrating an exterior of a slave robot that constitutes the surgical robot of FIG. 1.
Figure 3B:
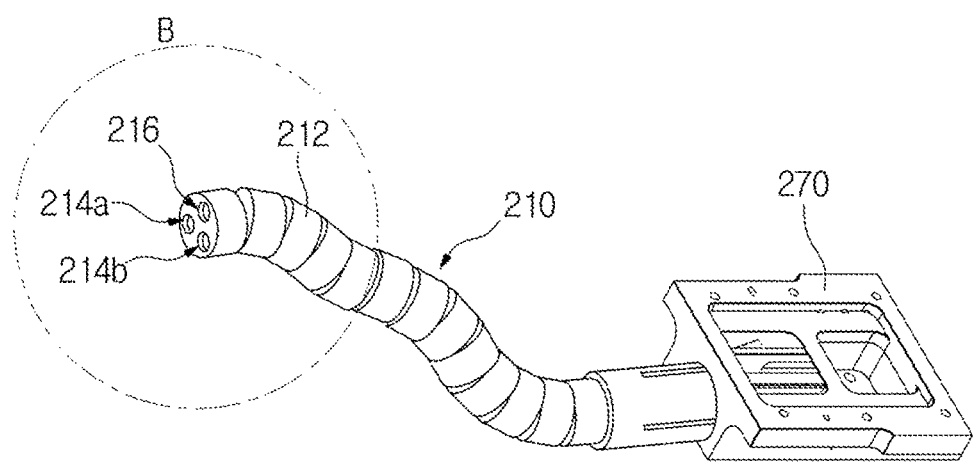
FIG. 3B illustrates a structure of a multi-tool module and a driving unit that are embedded in a casing.
Figure 3C:
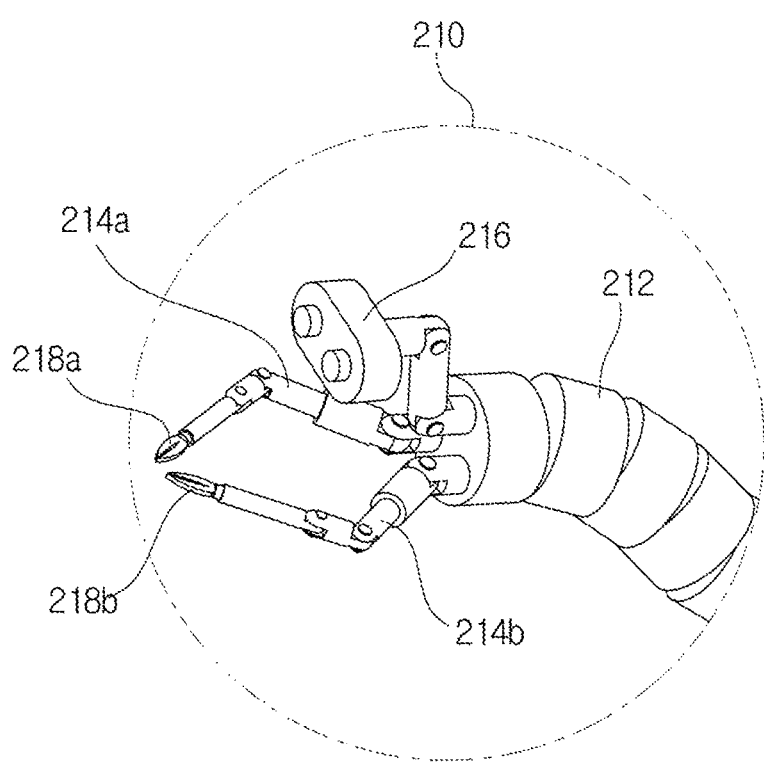
FIG. 3C is a planar view of two tools and one endoscope from a portion (a distal end of a guide tube) illustrated in FIG. 3B.

FIG. 3A is a perspective view illustrating an exterior of a slave robot that constitutes the surgical robot of FIG. 1, FIG. 3B illustrates a structure of a multi-tool module and a driving unit that are embedded in a casing, and FIG. 3C is a planar view of two tools and one endoscope from a portion B (a distal end of the guide tube 212) illustrated in FIG. 3B.

As illustrated in FIG. 3A, the slave robot 200 may include a body 201, the mounting arm 202 including a plurality of links and a plurality of joints, and the casing 208.

The body 201 of the slave robot 200 is an element for installing and supporting the mounting arm 202 that performs a surgical task, and a plurality of casters 201*a* is mounted on a bottom end of the body 201 so as to move the position of the slave robot 200. A lever (not shown) for changing operating states of the plurality of casters 201*a* may be disposed on each caster 201*a*. The manipulator may adjust the position of the lever so as to change the operating states of the casters 201*a*. The operating states of the casters 201*a* may include brake, free swivel, and directional lock or swivel lock.

The mounting arm 202 of the slave robot 200 includes three links (first through third links) 206*a* to 206*c* and three joints (first through third joints) 204*a* to 204*c*.

The first link 206*a* that constitutes the mounting arm 202 has a straight pillar shape and is disposed perpendicular to the body 201.

The first joint 204*a* that constitutes the mounting arm 202 is disposed on a connection part between the body 201 and the first link 206*a*. The first joint 204*a* may be implemented with a prismatic joint that moves along a designated axis among the x-axis, the y-axis, and the z-axis. The first joint 204*a* that is used to adjust x-, y-, and z-coordinates of a remote center of motion (RCM) for limitedly controlling an operation of the guide tube 212 inserted into the patient's body may have three degrees of freedom. In detail, the first joint 204*a* has three degrees of freedom including an x-axis translational motion, a y-axis translational motion, and a z-axis translation motion. To this end, an x-axis driving unit (not shown), a y-axis driving unit (not shown), and a z-axis driving unit (not shown) may be disposed on the first joint 204*a*.

The second link 206*b* is mechanically connected to a front end of the first link 206*a*. The second link 206*b* has a curve shape, as illustrated in FIG. 3. In detail, the second link 206*b* has the same shape as a part of a circular arc.

The second joint 204*b* is disposed on a connection part between the first link 206*a* and the second link 206*b*. The second joint 204*b* may be implemented with a revolute joint that rotates around the designated axis among the x-axis, the y-axis, and the z-axis. The second joint 204*b* that is an element for rotational motion of the casing 208 in which the guide tube 212 is embedded, may have two degrees of freedom. In detail, the second joint 204*b* has two degrees of freedom including roll direction rotation and pitch direction rotation of the casing 208. To this end, a roll driving unit (not shown) and a pitch driving unit (not shown) may be disposed on the second joint 204*b*.

The third link 206*c* is mechanically connected to a front end of the second link 206*b*. The third link 206*c* is formed in a ring shape, as illustrated in FIG. 3A. The casing 208 is disposed on an upper part of the third link 206*c*.

A multi-tool module 210 including the guide tube 212 connected to the mounting arm 202 and the plurality of tools 214*a* and 214*b* and the endoscope 216 disposed in the guide tube 212, and a driving unit 270 that drives elements (guide tube, a plurality of tools, and endoscope) of the multi-tool module 210 may be embedded in the casing 208 (see FIG.

3B). When the slave robot 200 does not perform surgery, as illustrated in FIG. 3A, the multi-tool module 210, i.e., the guide tube 212 including the plurality of tools 214a and 214b and the endoscope 216 is embedded in the casing 208 such that the guide tube 212 is not exposed to the outside. The casing 208 equipped with the guide tube 212 may be implemented to be mechanically separated from the third link 206c. In this way, when the casing 208 equipped with the guide tube 212 is separated from the third link 206c, the guide tube 212 used in surgery can be easily replaced or disinfected.

The third joint 204c is disposed at a connection part between the second link 206b and the third link 206c. The third joint 204c may be implemented with a revolute joint that rotates around the designated axis among the x-axis, the y-axis, and the z-axis. The third joint 204c that is an element for rotational motion of the casing 208 equipped with the guide tube 212 may have one degree of freedom. In detail, the third joint 204c has one degree of freedom including yaw direction rotation of the casing 208. To this end, a yaw driving unit (not shown) may be disposed on the third joint 204c.

As described above, when the slave robot 200 does not perform surgery, the multi-tool module 210 including the guide tube 212 illustrated in FIG. 3B and the plurality of tools 214a and 214b and the endoscope 216 disposed in the guide tube 212, and a driving unit 270 that is connected to the multi-tool module 210 and includes an actuator, such as a motor for driving each of elements of the multi-tool module 210, are embedded in the casing 208.

Meanwhile, a robot surgical procedure using the multi-tool module 210 including the guide tube 212, the plurality of tools 214a and 214b, and the endoscope 216 disposed in the guide tube 212 largely includes inserting the multi-tool module 210, positioning the multi-tool module 210, and performing an operation using the multi-tool module 210.

When the slave robot 200 performs surgery, the multi-tool module 210 embedded in the casing 208, more strictly, the guide tube 212 goes out of the casing 208 and is inserted into the body through the incision hole I formed in the patient's skin. In an operation of inserting the guide tube 212 into the body, like in the portion B of FIG. 3B, the multi-tool module 210 before the plurality of tools 214a and 214b and the endoscope 216 are extended from the guide tube 212, i.e., in a state in which the plurality of tools 214a and 214b and the endoscope 216 are folded in an internal space of the guide tube 212, is put into the patient's body.

If, after an operation of positioning the guide tube 212 inserted into the patient's body in the part on which an operation is to be performed (operating part) is performed, the guide tube 212 is close to the operating part, as illustrated in FIG. 3C, the plurality of tools 214a and 214b each having a distal end on which the end effectors 218a and 218b are mounted and one endoscope 216 are extended from the guide tube 212 so that the surgical task can be performed. FIG. 3C is a planar view of two tools (first and second tools 214a and 214b) and one endoscope 216 from the distal end (portion B of FIG. 3B) of the guide tube 212.

Some example embodiments may be directed to an integrated method of controlling operations of elements that constitute the slave robot 200 in the surgical robot having the slave robot 200 including the mounting arm 202, the guide tube 212 connected to the mounting arm 202, and the plurality of tools 214a and 214b and one endoscope 216 that are disposed within the guide tube 212 and extended from the guide tube 212 when the surgical task is performed, as illustrated in FIGS. 3A through 3C, using redundancy when the sum of degrees of freedom in a joint space of the elements, i.e., the mounting arm 202, the guide tube 212, the plurality of tools 214a and 214b, and one endoscope 216 is greater than the sum of degrees of freedom (degrees of freedom required for the task) in a task space of the elements, i.e., when the surgical robot (in particular, the slave robot) has redundancy.

In order to describe the concept of redundancy described above in more detail, first, it is premised that, in the slave robot 200 including the mounting arm 202, the guide tube 212 connected to the mounting arm 202, and the plurality of tools 214a and 214b and one endoscope 216 that are disposed within the guide tube 212 and extended from the guide tube 212 when the surgical task is performed, as illustrated in FIGS. 3A through 3C, each of the mounting arm 202, the guide tube 212, two tools 214a and 214b, and one endoscope 216 includes a plurality of links and a plurality of joints. Also, it is premised that the mounting arm 202 and the guide tube 212 operate while interacting with each other, the guide tube 212 and each of the tools 214a and 214b operate while interacting with each other, and the guide tube 212 and one endoscope 216 operate while interacting with each other. In some example embodiments, when the slave robot 200 is manufactured by implementing a degree of freedom a of the mounting arm 202 in the joint space as 6 (the sum of three degrees of translational freedom (3) in the x-, y-, and z-directions and three degrees of rotational freedom (3) in the roll, pitch, and yaw directions), a degree of freedom b of the guide tube 212 in the joint space as 6 (the sum of two of two degrees of bending freedom (2), one degree of freedom (1) in the insertion direction, and one degree of rotational freedom (1) in the roll direction), degrees of freedom c and d of each of the first and second tools 214a and 214b in the joint space as 6, and a degree of freedom e of the endoscope 216 in the joint space as 3 (three degrees of rotational freedom (3) in the roll, pitch, and yaw directions), a degree of freedom N of the slave robot 200 including all of the above-described elements in the joint space is 27 (N=a+b+c+d+e=6+6+6+6+3=27).

Meanwhile, a degree of freedom in the task space required for performing an arbitrary task using a mechanism unit (for example: tool or endoscope) including a plurality of joints in the 3D space including the x-axis, the y-axis, and the z-axis is 6 that is the sum of three degrees of translational freedom (3) in the x-, y-, and z-directions and three degrees of rotational freedom (3) in the roll, pitch, and yaw directions.

In the slave robot 200 including two tools 214a and 214b and one endoscope 216 illustrated in FIGS. 3A through 3C, when degrees of freedom f and g in the task space of each of the first and second tools 214a and 214b, i.e., a degree of freedom in the task space required for the surgical operation is 6 and a degree of freedom h in the task space of the endoscope 216 is 3 (only degrees of rotational freedom in the roll, pitch, and yaw directions are required), a degree of freedom M in the task space of the slave robot 200 including two tools 214a and 214b and one endoscope 216 is 15 (M=f+g+h=6+6+3=15).

When a degree of freedom N of a multi-joint robot in the joint space is greater than a degree of freedom M of the multi-joint robot in the task space, redundancy occurs. Since the degree of freedom (N=27) of the slave robot 200 described above in the joint space is greater than the degree of freedom (M=15) of the slave robot 200 in the task space, the slave robot 200 may be a system having redundancy. Some example embodiments may be directed to a procedure of obtaining a solution in a joint space of each of elements that constitute the slave robot 200, i.e., the mounting arm 202, the guide tube 212, the plurality of tools 214a and 214b, and the endoscope 216 extended from the guide tube 212, so as to achieve several objectives using this redundancy. In some example embodiments, the solution in each joint space of each of the mounting arm 202, the guide tube 212, the plurality of tools 214a and 214b, and the endoscope 216 that constitute the slave robot 200 is a desired rotational angle of each of a plurality of joints that constitute the mounting arm 202, a desired rotational angle of each of a plurality of joints that constitute the guide tube 212, a desired rotational angle of each of a plurality of joints that constitute the plurality of tools 214a and 214b, and a desired rotational angle of each of a plurality of joints that constitute the endoscope 216, which are calculated in each control period so as to perform the surgical task.

Figure 4:
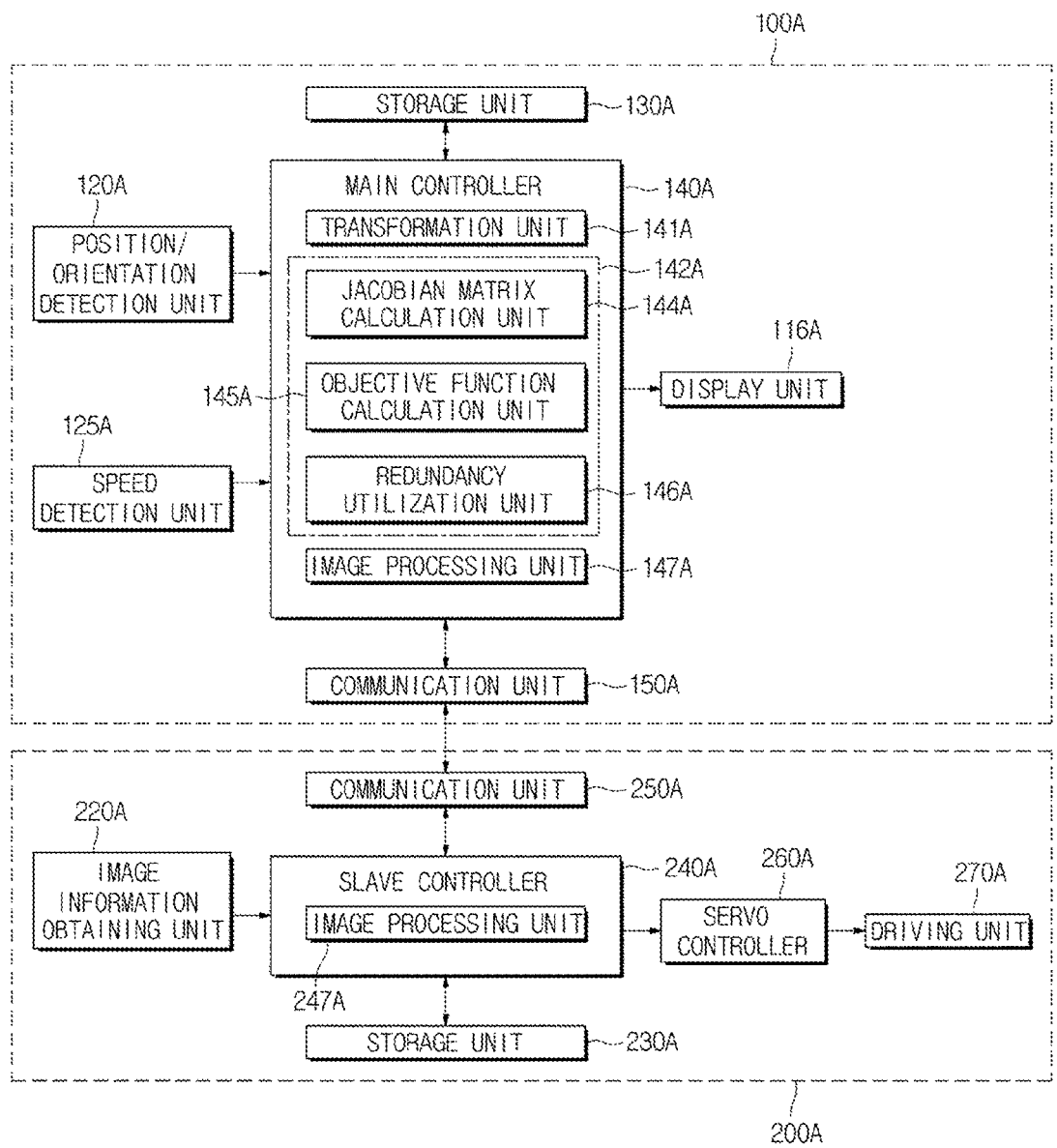
FIG. 4 is a control block diagram of a surgical robot in accordance with some example embodiments.

FIG. 4 is a control block diagram of a surgical robot in accordance with some example embodiments.

As illustrated in FIG. 4, the surgical robot includes a master device 100A and a slave robot 200A.

In some example embodiments, it is premised that each of a mounting arm 202, a guide tube 212, a plurality of tools 214a and 214b, and an endoscope 216 that constitute the slave robot 200A includes a plurality of links and a plurality of joints. Also, in some example embodiments, it is premised that the mounting arm 202 and the guide tube 212 operate while interacting with each other, the guide tube 212 and each of the plurality of tools 214a and 214b operate while interacting with each other, and the guide tube 212 and one endoscope 216 operate while interacting with each other. Furthermore, a premise of some example embodiments is a case that the slave robot 200A has redundancy, i.e., when the degree of freedom N of the slave robot 200A in the joint space is greater than the degree of freedom M of the slave robot 200A in the task space (N>M).

The master device 100A may include a position/orientation detection unit 120A, a speed detection unit 125A, a storage unit 130A, a main controller 140A, a communication unit 150A, and a display unit 116A.

The position/orientation detection unit 120A detects position and orientation of the master manipulation units 112L and 112R manipulated by the manipulator. When the master manipulation units 112L and 112R are implemented to have six degrees of freedom, position information of the master manipulation units 112L and 112R may be represented as (x', y', z'), and orientation information of the master manipulation units 112L and 112R may be represented as ($\alpha'$, $\beta'$, $\gamma'$). The position/orientation detection unit 120A includes a rotational angle sensor (not shown) that is mounted on each of a plurality of joints connected to the master manipulation units 112L and 112R and detects a rotational angle of each joint and an arithmetic operation module that calculates position and orientation information in the 3D space of the master manipulation units 112L and 112R by substituting a rotational angle of each joint detected by the rotational angle sensor by an equation of forward kinematics of the master manipulation units 112L and 112R. The rotational angle sensor may be an encoder or a potentiometer. In some example embodiments, the position/orientation detection unit 120A including the rotational angle sensor and the arithmetic operation module has been described. However, any device that may detect information regarding positions and orientations of the master manipulation units 112L and 112R may be used as the position/orientation detection unit 120A.

The speed detection unit 125A is mounted on each of the plurality of joints connected to the master manipulation units 112L and 112R and detects speed of the master manipulation units 112L and 112R, more specifically, a rotational speed of each of joints connected to the master manipulation units 112L and 112R. A tachometer may be used as the speed detection unit 125A. In some example embodiments, the speed of the master manipulation units 112L and 112R is detected using the speed detection unit 125A. However, the speed of the master manipulation units 112L and 112R may be calculated by differentiating an output value of the rotational angle sensor (for example, encoder) that constitutes the position/orientation detection unit 120A without using an additional speed detection unit (speed sensor), and calculated speed information may be used.

The storage unit 130A is a memory in which information and an algorithm required to calculate a solution in the joint space, i.e., a desired rotational angle of each of joints that constitute the mounting arm 202, the guide tube 212, the plurality of tools 214a and 214b, and the endoscope 216 using redundancy of the slave robot 200A are stored. A scaling factor applied when motion scaling between an operation of the master manipulation units 112L and 112R of the master device 100A and an operation of a distal end (a plurality of tools and endoscope) of the slave robot 200A is performed, an algorithm required to calculate a Jacobian matrix, information regarding a kinematics structure of the slave robot 200A, a plurality of individual objective functions for achieving a plurality of individual objectives required to calculate an objective function, the result of learning regarding a plurality of operations that constitute a surgical task, and weights multiplied with individual objective functions depending on the type of the surgical task are stored in the storage unit 130A.

Also, the storage unit 130A may store various reference images, such as an X-ray image captured before an operation is performed, a computed tomography (CT) image, and a magnetic resonance imaging (MRI) image.

The main controller 140A that is a processor for controlling the overall operation of the surgical robot includes a transformation unit 141A, a redundancy inverse kinematics interpretation unit 142A, and an image processing unit 147A.

The transformation unit 141A transforms position and orientation information x', y', z', $\alpha'$, $\beta'$, and $\gamma'$ of the master manipulation units 112L and 112R detected by the position/orientation detection unit 120A into motion instruction information in the task space of the slave robot 200A, i.e., the manipulator's desired position and orientation information x, y, z, $\alpha$, $\beta$, and $\gamma$ of the distal end (distal end of each of the plurality of tools and a distal end of the endoscope) of the slave robot 200A. The transformation unit 141A may transform the position and orientation information x', y', z', $\alpha'$, $\beta'$, and $\gamma'$ of the master manipulation units 112L and 112R into the motion instruction information x, y, z, $\alpha$, $\beta$, and $\gamma$ in the task space of the slave robot 200A using motion scaling between the operation of the master manipulation units 112L and 112R of the master device 100A and the operation of the distal end (a plurality of tools and endoscope) of the slave robot 200A. That is, the transformation unit 141A may calculate the motion instruction information x, y, z, $\alpha$, $\beta$, and $\gamma$ in the task space of the slave robot 200A by multiplying the position and orientation information x', y', z', $\alpha'$, $\beta'$, and $\gamma'$ of the master manipulation units 112L and 112R by the scaling factor applied when motion scaling is performed.

The redundancy inverse kinematics interpretation unit 142A that is an element for generating a control signal (desired rotational angle of each of a plurality of joints that constitute each element) for an integrated method of controlling operations of elements (mounting arm, guide tube, a plurality of tools, and endoscope) of the slave robot 200A using redundancy of the slave robot 200A includes a Jacobian matrix calculation unit 144A, an objective function calculation unit 145A, and a redundancy utilization unit 146A.

Before describing the elements of the redundancy inverse kinematics interpretation unit 142A in detail, first, the concept of forward kinematics and inverse kinematics and interpretation of inverse kinematics of the slave robot 200A having redundancy will now be described.

In general, forward kinematics in a robot system is to obtain position and orientation (task variable p) on an orthogonal coordinate system of a robot distal end when a series of joint angles (joint variable q) are given. Forward kinematics is relatively simpler than inverse kinematics, and a solution of forward kinematics can be obtained using homogeneous transform. Meanwhile, in contrast to forward kinematics, inverse kinematics is to obtain joint angles (joint variable q) when the position and orientation (task variable p) on the orthogonal coordinate system of the robot distal end are given, i.e., to express a task defined in the task space as movement in the joint space. Since a kinematics equation is a nonlinear equation comprised of a transcendental function, it may be relatively more difficult or impossible to obtain the solution than in forward kinematics. Also, there may be no solution or several solutions.

As premised above, in case of the slave robot 200A having redundancy, inverse kinematics interpretation can be numerically performed using a pseudo-inverse matrix of Jacobian. Hereinafter, inverse kinematics interpretation of redundancy will be described in more detail.

Inverse kinematics is a procedure in which a rotational angle of a joint corresponding to position and orientation of a distal end of a manipulator (in some example embodiments, orientation is expressed as Euler angles) when the position and orientation of the distal end of the manipulator are given. There is no particular method for obtaining an inverse kinematics solution at a position level, and the inverse kinematics solution needs to be obtained using a geometric interaction formula or depending on intuition according to a joint structure of the given robot. In case of a surgical robot or a humanoid robot having a large number of joints, the inverse kinematics solution may not be found at the position level. In some example embodiments, an inverse matrix is calculated using a Jacobian interaction formula at a speed level in real-time, and a speed of each joint is obtained and then, the speed is numerically integrated, thereby determining the inverse kinematics solution.

In a system having redundancy, such as the slave robot 200A described above, the relationship between the position and orientation on the orthogonal coordinate system of the robot distal end (each distal end of a plurality of tools and a distal end of an endoscope), i.e., a task variable p and a series of joint angles in the joint space, i.e., a joint variable q may be represented using the following Equation 1.

$$p = f(q) \quad \text{[Equation 1]}$$

In some example embodiments, $p \in R^M$, $q \in R^N$, $M<N$, N is a degree of freedom of the slave robot 200A having redundancy in the joint space, and M is a degree of freedom of the slave robot 200A having redundancy in the task space.

In some example embodiments, $p \in R^M$ means that the task variable p may be represented as an M×1 matrix. For example, when position information $x_1$, $y_1$, and $z_1$ and orientation information $\alpha_1$, $\beta_1$, and $\gamma_1$ of a distal end of the first tool 214a having six degrees of freedom in the task space, position information $x_2$, $y_2$, and $z_2$ and orientation information $\alpha_2$, $\beta_2$, and $\gamma_2$ of a distal end of the second tool 214b having six degrees of freedom in the task space, and orientation information $\alpha_3$, $\beta_3$, and $\gamma_3$ of a distal end of the endoscope 216 having three degrees of freedom in the task space are the task variable p (a degree of freedom in the task space M=6+6+3=15), the task variable p may be represented as the following 15×1 matrix.

$$p = \begin{bmatrix} x_1 \\ y_1 \\ z_1 \\ \alpha_1 \\ \beta_1 \\ \gamma_1 \\ \vdots \\ \alpha_3 \\ \beta_3 \\ \gamma_3 \end{bmatrix}$$

Also, $q \in R^N$ means that the joint variable q may be represented as an N×1 matrix. For example, when rotational angle information $q_1$, $q_2$, $q_3$, $q_4$, $q_5$, and $q_6$ of six joints that constitute the mounting arm 202 having six degrees of freedom in the joint space, rotational angle information $q_7$, $q_8$, $q_9$, $q_{10}$, $q_{11}$, and $q_{12}$ of six joints that constitute the guide tube 212 having six degrees of freedom in the joint space, rotational angle information $q_{13}$, $q_{14}$, $q_{15}$, $q_{16}$, $q_{17}$, and $q_{18}$ of six joints that constitute the first tool 214a having six degrees of freedom in the joint space, rotational angle information $q_{19}$, $q_{20}$, $q_{21}$, $q_{22}$, $q_{23}$, and $q_{24}$ of six joints that constitute the second tool 214b having six degrees of freedom in the joint space, and rotational angle information $q_{25}$, $q_{26}$, and $q_{27}$ of three joints that constitute the endoscope 216 having three degrees of freedom in the joint space are a joint variable q (a degree of freedom in the joint space N=6+6+6+6+3=27), the joint variable q may be represented as the following 27×1 matrix.

$$q = \begin{bmatrix} q_1 \\ q_2 \\ q_3 \\ q_4 \\ q_5 \\ q_6 \\ \vdots \\ q_{25} \\ q_{26} \\ q_{27} \end{bmatrix}$$

By differentiating the above-described Equation 1 in relation to time, the following Equation 2 that is a differential kinematics equation can be calculated.

$$\dot{p} = J(q)\dot{q} \quad \text{[Equation 2]}$$

In some example embodiments, J(q) is a Jacobian matrix of f(q).

Since the joint variable q is obtained through inverse kinematics interpretation, the above-described Equation 2 can be summarized as an equation of a speed vector $\dot{q}$ of a joint, as shown in Equation 3.

$$\dot{q} = J^{-1}(q)\dot{p} \quad \text{[Equation 3]}$$

When the degree of freedom N in the joint space is the same as the degree of freedom M in the task space (N=M), i.e., when the system has no redundancy, an inverse matrix $J^{-1}(q)$ of the Jacobian matrix J(q) may be calculated, and a speed (elements of the speed vector $\dot{q}$ of the joint, i.e., $\dot{q}_1$, $\dot{q}_2$, ...) of each joint may be calculated by substituting the inverse matrix $J^{-1}(q)$ by Equation 3, and then, the speed may be integrated so as to calculate a rotational angle (elements of the joint variable q, i.e., $q_1$, $q_2$, ...) of each joint.

Meanwhile, when the degree of freedom N in the joint space is greater than the degree of freedom M in the task space, i.e., when the system has redundancy, like in the above-described slave robot 200A, the number of columns of the Jacobian matrix J(q) is more than the number of rows of the Jacobian matrix J(q) and thus the inverse matrix $J^{-1}(q)$ of the Jacobian matrix cannot be calculated, and there is an infinite inverse kinematics solution.

Thus, when the system has redundancy, the inverse kinematics solution is calculated using a pseudo-inverse matrix $J^{\#}(q)$ of the Jacobian matrix J(q). An equation in which a speed (speed vector $\dot{q}$ of the joint) of each joint in the joint space is calculated using the pseudo-inverse matrix $J^{\#}(q)$ of the Jacobian matrix J(q), may be represented as the following Equation 4, and the pseudo-inverse matrix $J^{\#}(q)$ of the Jacobian matrix J(q) may be represented as the following Equation 5.

$$\dot{q}=J^{\#}\dot{p}+(I_n-J^{\#}J)r \quad \text{[Equation 4]}$$

$$J^{\#}=J^T(JJ^T)^{-1} \quad \text{[Equation 5]}$$

In some example embodiments, $I_n$ is an n×n unit matrix (or identity matrix), r is an arbitrary vector, and $(I_n-J^{\#}J)$ is a null space of a vector r.

Various methods of defining the arbitrary vector r(q) so as to utilize redundancy may be defined as the following Equation 6, for example.

$$r = -k\frac{\partial w}{\partial q} \quad \text{[Equation 6]}$$

In some example embodiments, k is a constant, and w is an objective function or a performance index an evaluation function.

The objective function w in which an objective of the system (in some example embodiments, to enlarge a workspace of tools and to minimize a possibility of collision between the tools and a peripheral obstacle) is quantitatively set in consideration of all conditions, is a significant base in quantitative evaluation of optimization of the system or achievement of the objective. That is, the objective function w is an index (index for evaluating the system) that is set to quantitatively evaluate suitability of the system in design, manipulation, and operation of a control system and an industrial system, and a solution in which a set objective function value is maximized or minimized (a desired rotational angle of each of a plurality of joints), needs to be found among solutions satisfying a system model (in some example embodiments, a solution in the joint space and a desired rotational angle vector q of each of a plurality of joints that constitute the mounting arm 202, the guide tube 212, the plurality of tools 214a and 214b, and the endoscope 216) so as to quantitatively perform optimal design or control of the system.

In some example embodiments, if the solution in the joint space in which the objective function w is minimized, is found, optimal control of the system (surgical robot) that utilizes redundancy of the slave robot 200A can be performed. The objective function w (hereinafter, w is referred to as an objective function of the whole system) may be represented as a weighted sum of a plurality of objective functions $w_1$ to $w_n$ (hereinafter, $w_1$ to $w_n$ are referred to as individual objective functions). Examples of the individual objective functions $w_1$ to $w_n$ may include a reciprocal number of a distance between each of the tools 214a and 214b and a joint limit, a reciprocal number of a distance between each of the tools 214a and 214b and a singular pose, a joint torque square sum, and a reciprocal number of a distance between each of the tools 214a and 214b and a peripheral obstacle.

Hereinafter, some example embodiments will be described in more detail with reference to FIGS. 5 through 9.

Figure 5:
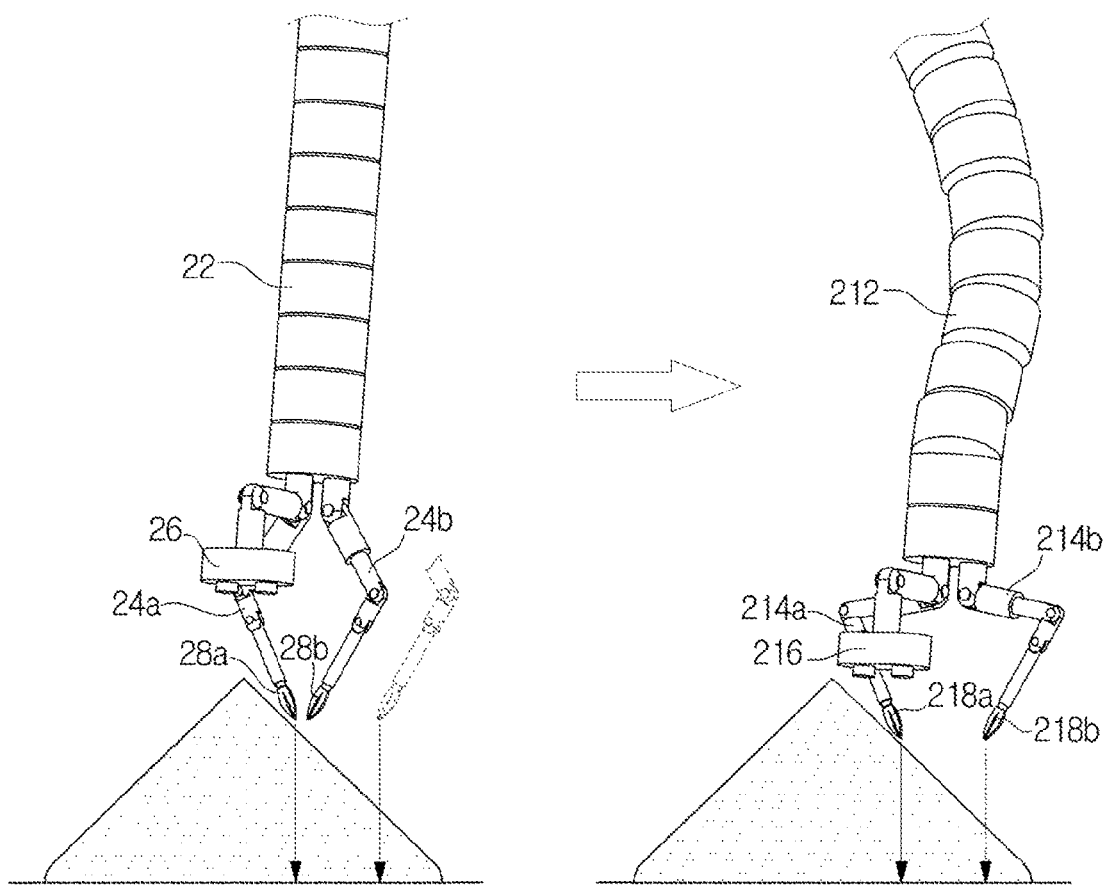
FIG. 5 is a conceptual view illustrating extension of a workspace of tools achieved by some example embodiments.

FIG. 5 is a conceptual view illustrating extension of a workspace of tools (including an endoscope) achieved by some example embodiments.

The left drawing of FIG. 5 illustrates a case that a surgical task is performed using an existing tool controlling method, and the right drawing of FIG. 5 illustrates a case that the surgical task is performed using a tool controlling method according to some example embodiments.

When the surgical task is performed using a rigid (inflexible) fixed type guide tube or a rod-shaped guide tube according to the related art or even when the surgical task is performed using a guide tube 22 that is flexible and has multiple degrees of freedom, as illustrated on the left side of FIG. 5, the guide tube 22 and each of tools (a first tool 24a and a second tool 24b), which are extended from the guide tube 22 and have distal ends on which end effectors 28a and 28b are mounted, operate individually, and the guide tube 22 and an endoscope 26 extended from the guide tube 22 operate individually. Thus, each of the tools 24a and 24b and/or the endoscope 26 may reach the joint limit while the surgical task is performed, or a state (a locked state) in which the plurality of tools 24a and 24b are in a singular pose and cannot be moved to a desired position or orientation, occurs. That is, if each of the tools 24a and 24b and/or the endoscope 26 reaches the joint limit or corresponds to the singular pose, each of the tools 24a and 24b and/or the endoscope 26 cannot be implemented due to a limitation in the workspace of the tools 24a and 24b. When points indicated by arrows on the left side of FIG. 5 are desired poses of the first and second tools 24a and 24b and a portion indicated by dotted lines illustrates a case that the second tool 24b is moved to the desired pose, if the second tool 24b reaches the joint limit or corresponds to the singular pose, the second tool 24b cannot be moved to the desired pose. (the second tool 24b cannot be moved to a region indicated by dotted lines.)

Meanwhile, since in some example embodiments, as illustrated on the right side of FIG. 5, the surgical task is performed using the guide tube 212 that is flexible and has multiple degrees of freedom, the guide tube 212 and each of the tools (the first tool 214a and the second tool 214b), which are extended from the guide tube 212 and have distal ends on which the end effectors 218a and 218b are mounted, operate while interacting with each other, the guide tube 212 and the endoscope 216 extended from the guide tube 212 operate while interacting with each other, and operations of elements of the slave robot 200A can be controlled in an integrated manner using redundancy of the slave robot 200A, even an operation in which, when the existing guide tube and tool controlling method (individual operation control) is applied, the guide tube 22 and the tools 24a and 24b cannot be implemented due to a limitation in the workspace of the tools 24a and 24b (including the endoscope 26), can be performed. When points indicated by arrows on the right side of FIG. 5 are desired poses of the first tool 214a and the second tool 214b, in some example embodiments, the guide tube 212 and the second tool 214b operate while interacting with each other. Thus, in order to move the second tool 214b to the desired pose, the second tool 214b is controlled to be moved in a direction (right direction) corresponding to the desired pose and simultaneously, the guide tube 212 is also controlled to be moved in a direction in which the second tool 214b may easily reach the desired pose. (the guide tube 212 is bent in the right direction that is a direction corresponding to the desired pose of the second tool 214b.)

When an individual objective function for achieving individual objectives to enlarge the workspace of the tools described with reference to FIG. 5 is $w_1$, the individual objective function $w_1$ may be defined as a reciprocal number 1/d1 of a distance d1 between each of the tools 214a and 214b and the joint limit or a reciprocal number 1/d2 of a distance d2 between the endoscope 216 and the joint limit ($w_1$=1/d1 or $w_1$=1/d2) or as a reciprocal number 1/d3 of a distance d3 between each of the tools 214a and 214b and the singular pose or a reciprocal number 1/d4 of a distance d4 between the endoscope 216 and the singular pose ($w_1$=1/d3 or 1/d4). Also, the individual objective function $w_1$ may be defined as a simple sum or a weighted sum of the reciprocal number 1/d1 of the distance between each of the tools 214a and 214b and the joint limit (or the reciprocal number 1/d2 of the distance between the endoscope 216 and the joint limit) and the reciprocal number 1/d3 of the distance between each of the tools 214a and 214b and the singular pose (or the reciprocal number 1/d4 of the distance between the endoscope 216 and the singular pose). In some example embodiments, when the distance d1 between each of the tools 214a and 214b and the joint limit (or the distance d1 between the endoscope 216 and the joint limit) or the distance d3 between each of the tools 214a and 214b and the singular pose (or the distance d4 between the endoscope 216 and the singular pose) is maximized, the workspace of the tools 214a and 214b can be enlarged to the maximum. In terms of the individual objective function w1, when the individual objective function w1 is minimized, the workspace of the tools 214a and 214b can be enlarged to the maximum.

Figure 6:
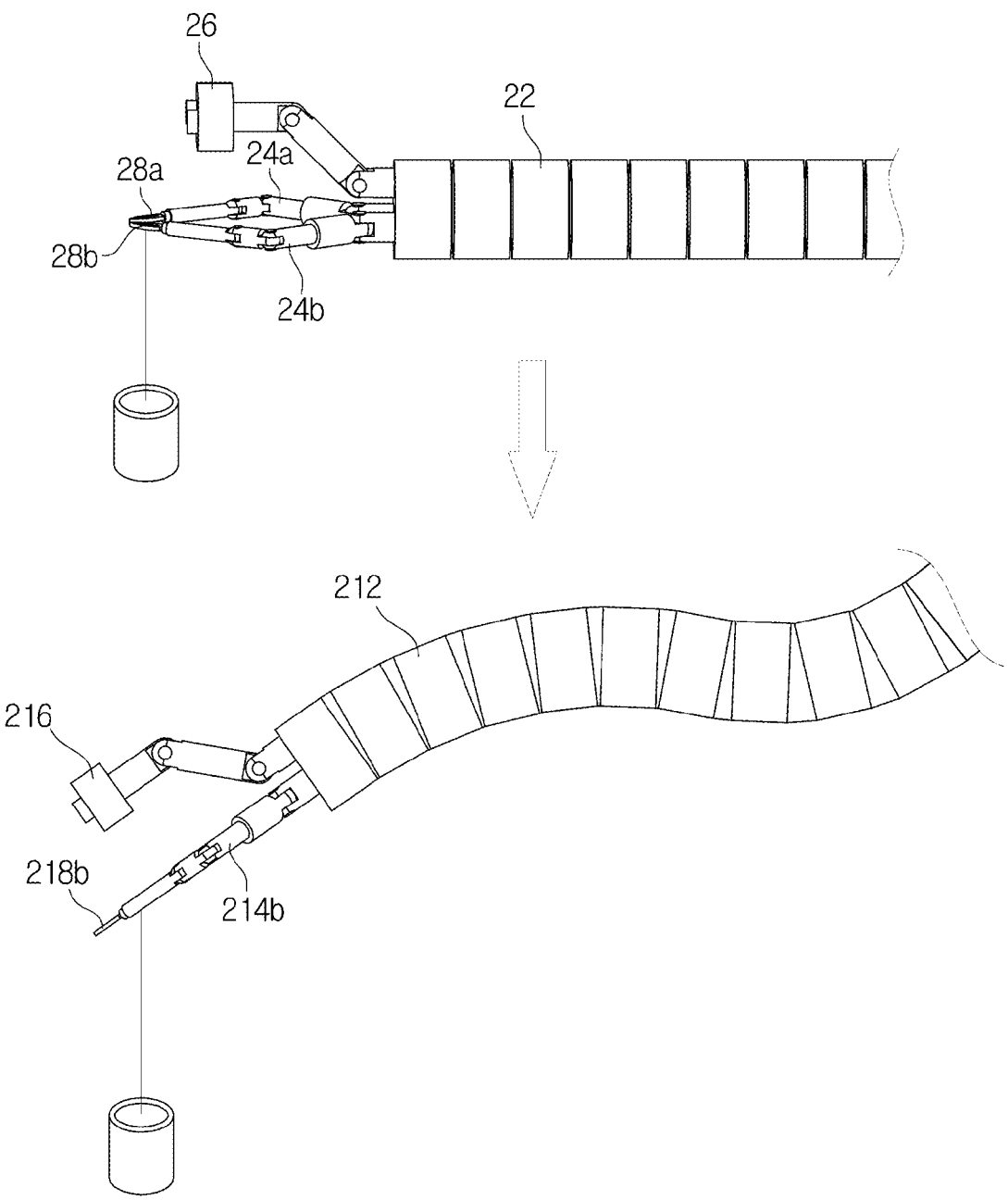
FIG. 6 is a conceptual view illustrating minimization of rigidity required for joints of the tools achieved by some example embodiments.

FIG. 6 is a conceptual view illustrating minimization of rigidity required for joints of the tools (including the endoscope) achieved by some example embodiments.

The upper drawing of FIG. 6 illustrates a case that a surgical task is performed using an existing tool controlling method, and the lower drawing of FIG. 6 illustrates a case that the surgical task is performed using a tool controlling method according to some example embodiments.

When the surgical task is performed using a rigid (inflexible) fixed type guide tube or a rod-shaped guide tube according to the related art or even when the surgical task is performed using the guide tube 22 that is flexible and has multiple degrees of freedom, as illustrated on the upper side of FIG. 6, the guide tube 22 and each of the tools (the first tool 24a and the second tool 24b), which are extended from the guide tube 22 and have distal ends on which the end effectors 28a and 28b are mounted, operate individually, and the guide tube 22 and the endoscope 26 extended from the guide tube 22 operate individually. Thus, an excessive payload is applied to parts of a plurality of joints that constitute each of the tools 24a and 24b and the endoscope 26 while the surgical task is performed, and rigidity (rigidity required for each joint) required for each of joints that constitute the plurality of tools 24a and 24b and the endoscope 26 increases. When a cylindrical object illustrated on the upper side of FIG. 6 is the payload applied to the plurality of tools 24a and 24b and the endoscope 26, on the upper side of FIG. 6, the payload is applied to a distal end of the second tool 24b so that rigidity required for each of joints that constitute the plurality of tools 24a and 24b and the endoscope 26 increases.

Meanwhile, since in some example embodiments, as illustrated on the lower side of FIG. 6, the surgical task is performed using the guide tube 212 that is flexible and has multiple degrees of freedom, the guide tube 212 and each of the tools (the first tool 214a and the second tool 214b), which are extended from the guide tube 212 and have distal ends on which the end effectors 218a and 218b are mounted, operate while interacting with each other, the guide tube 212 and the endoscope 216 extended from the guide tube 212 operate while interacting with each other, and operations of elements of the slave robot 200A can be controlled in an integrated manner using redundancy of the slave robot 200A, rigidity required for each of joints that constitute the plurality of tools 214a and 214b and the endoscope 216 can be reduced by distribution of the payload.

When an individual objective function for achieving individual objectives to minimize rigidity required for each of joints of the tools described with reference to FIG. 6 is $w_2$, the individual objective function $w_2$ may be defined as a joint torque square sum of torque squares ($\tau_1^2$, $\tau_2^2$, $\tau_3^2$ ... ) of each of joints that constitute the plurality of tools 214a and 214b and the endoscope 216 ($w_2=\tau_1^2+\tau_2^2+\tau_3^2+$ ... ). In some example embodiments, when the joint torque square sum of the torque squares ($\tau_1^2$, $\tau_2^2$, $\tau_3^2$ ... ) of each of joints that constitute the plurality of tools 214a and 214b and the endoscope 216, i.e., the individual objective function $w_2$ is minimized, rigidity required for each of joints that constitute the plurality of tools 214a and 214b and the endoscope 216 can be minimized.

Figure 7:
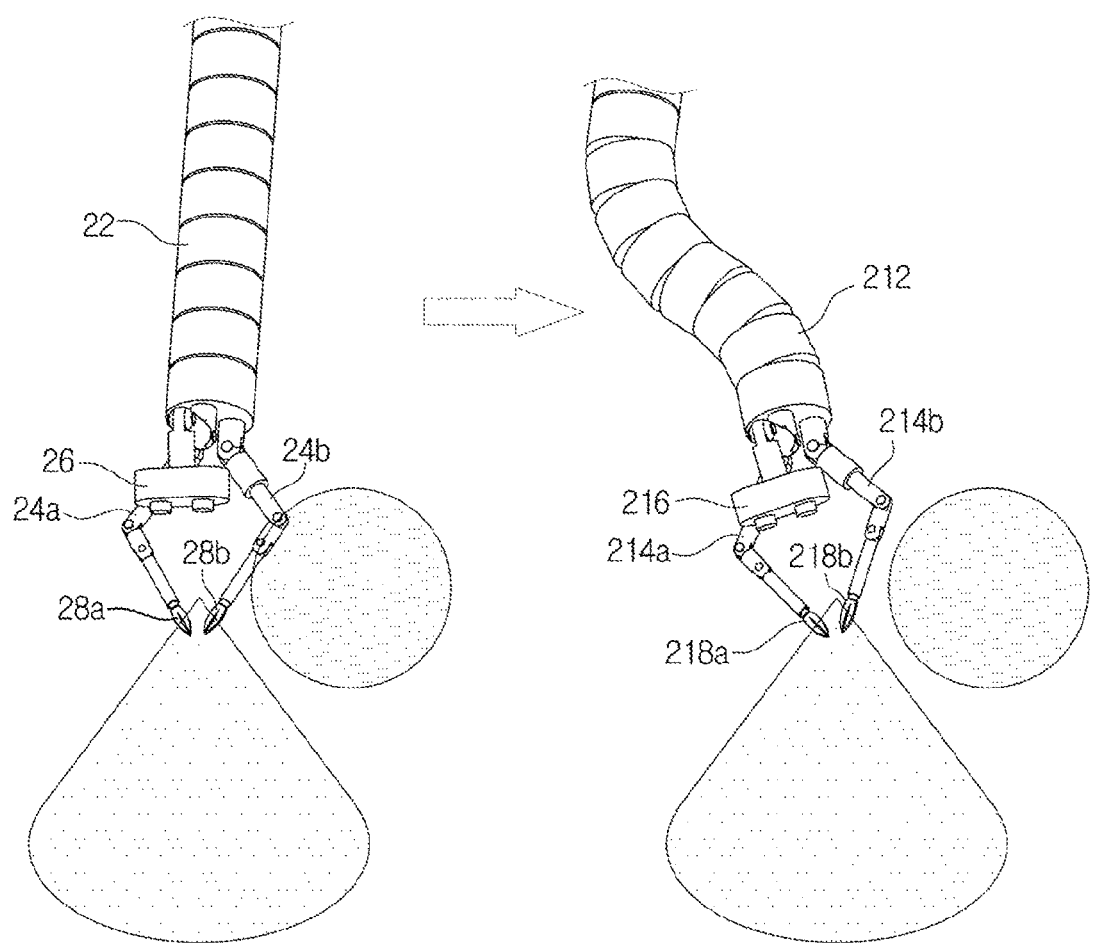
FIG. 7 is a conceptual view illustrating minimization of a possibility of collision between tools and a peripheral obstacle achieved by some example embodiments.

FIG. 7 is a conceptual view illustrating minimization of a possibility of collision between tools (including the endoscope) and a peripheral obstacle achieved by some example embodiments.

The left drawing of FIG. 7 illustrates a case that a surgical task is performed using an existing tool controlling method, and the right drawing of FIG. 7 illustrates a case that the surgical task is performed using a tool controlling method according to some example embodiments.

When the surgical task is performed using a rigid (inflexible) fixed type guide tube or a rod-shaped guide tube according to the related art or even when the surgical task is performed using the guide tube 22 that is flexible and has multiple degrees of freedom, as illustrated on the left side of FIG. 7, the guide tube 22 and each of the tools (the first tool 24a and the second tool 24b), which are extended from the guide tube 22 and have distal ends on which the end effectors 28a and 28b are mounted, operate individually, and the guide tube 22 and the endoscope 26 extended from the guide tube 22 operate individually. Thus, collision with the peripheral obstacle (a human body tissue or other tools) occurs inevitably so that each of the tools 24a and 24b and/or the endoscope 26 can be moved to desired poses while the surgical task is performed. When, on the left side of FIG. 7, a direction in which the end effector 28b mounted on the second tool 24b is disposed, is a desired pose, collision with the peripheral obstacle is accompanied so that the second tool 24b can be moved to the desired pose.

Meanwhile, since in some example embodiments, as illustrated on the right side of FIG. 7, the surgical task is performed using the guide tube 212 that is flexible and has multiple degrees of freedom, the guide tube 212 and each of the tools (the first tool 214a and the second tool 214b), which are extended from the guide tube 212 and have distal ends on which the end effectors 218a and 218b are mounted, operate while interacting with each other, the guide tube 212 and the endoscope 216 extended from the guide tube 212 operate while interacting with each other, and operations of elements of the slave robot 200A can be controlled in an integrated manner using redundancy of the slave robot 200A, collision between each of the tools 214a and 214b and the peripheral obstacle and/or collision between the endoscope 216 and the peripheral obstacle can be avoided, or a possibility of collision with the peripheral obstacle can be reduced. When, on the right side of FIG. 7, a direction in which the end effector 218b mounted on the second tool 214b is disposed, is a desired pose, in some example embodiments, the guide tube 212 and the second tool 214b operate while interacting with each other. Thus, in order to avoid collision between the second tool 214b and the peripheral obstacle, the second tool 214b is controlled to be moved in a direction (left direction) in which the second tool 214b is far away from the peripheral obstacle and simultaneously, the guide tube 212 is also controlled to be moved in a direction in which the second tool 214b may be easily far away from the peripheral obstacle. (the guide tube 212 is bent in an S-shape so as to prevent collision between the second tool 214b and the peripheral obstacle.)

When an individual objective function for achieving an individual objective to minimize a possibility of collision between a tool and the peripheral obstacle described with reference to FIG. 7 is $w_3$, the individual objective function $w_3$ may be defined as a distance between each of the tools 214a and 214b and the peripheral obstacle or a reciprocal number $1/d_3$ of a distance $d_3$ between the endoscope 216 and the peripheral obstacle ($w_3 = 1/d_3$). In some example embodiments, when the distance between each of the tools 214a and 214b and the peripheral obstacle or the distance $d_3$ between the endoscope 216 and the peripheral obstacle is maximized, a possibility of collision between the tool and the peripheral obstacle can be minimized. In terms of the individual objective function $w_3$, when the individual objective function $w_3$ is minimized, a possibility of collision between the tool and the peripheral obstacle can be minimized.

Figure 8:
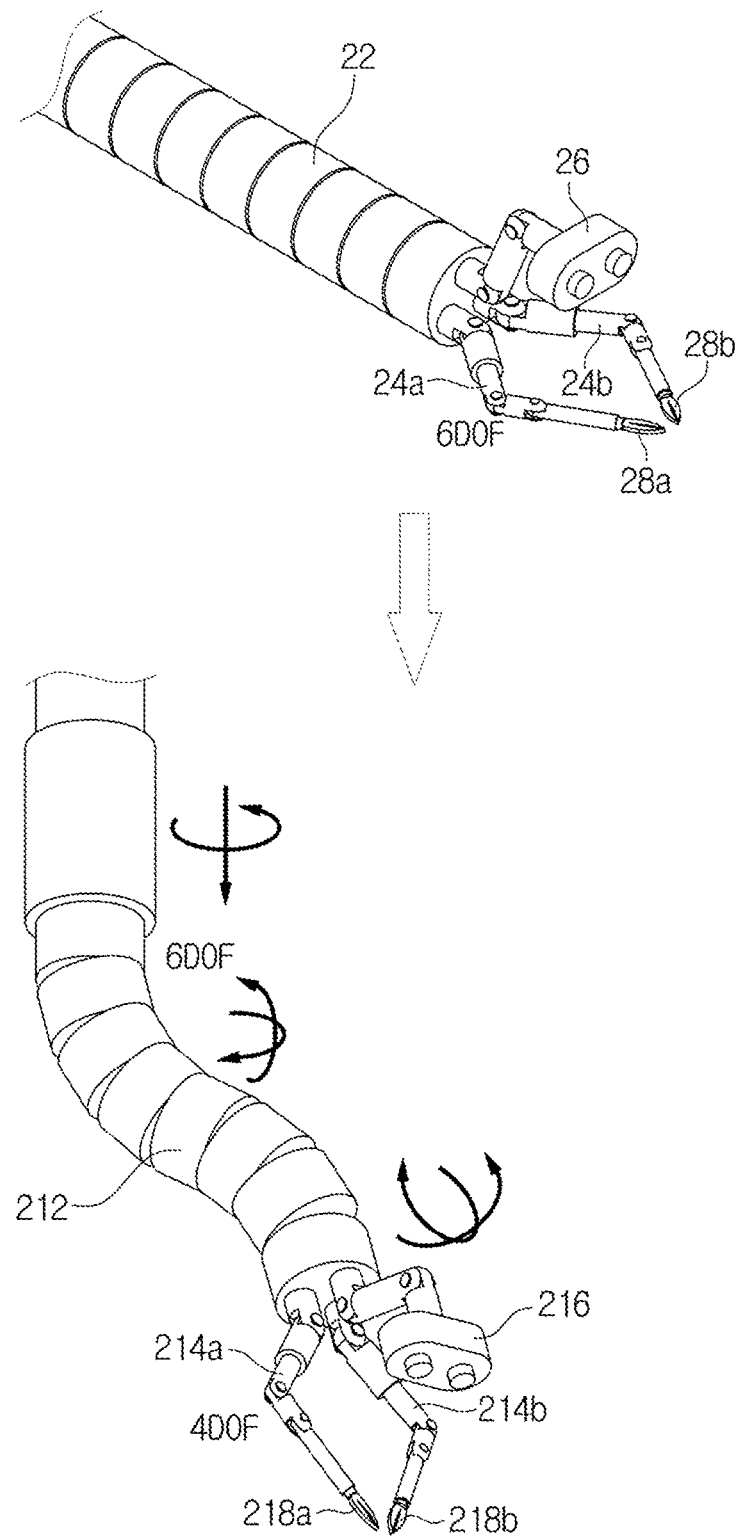
FIG. 8 is a conceptual view illustrating minimization of a degree of freedom required for tools achieved by some example embodiments.

FIG. 8 is a conceptual view illustrating minimization of a degree of freedom required for tools achieved by some example embodiments.

The upper drawing of FIG. 8 illustrates a case that a surgical task is performed using an existing tool controlling method, and the lower drawing of FIG. 8 illustrates a case that the surgical task is performed using a tool controlling method according to some example embodiments.

When the surgical task is performed using a rigid (inflexible) fixed type guide tube or a rod-shaped guide tube according to the related art or even when the surgical task is performed using the guide tube 22 that is flexible and has multiple degrees of freedom, as illustrated on the upper side of FIG. 8, the guide tube 22 and each of the tools (the first tool 24a and the second tool 24b), which are extended from the guide tube 22 and have distal ends on which the end effectors 28a and 28b are mounted, operate individually, and the guide tube 22 and the endoscope 26 extended from the guide tube 22 operate individually. Thus, in order to perform the surgical task, both each of the tools 24a and 24b and the endoscope 26 are required to be implemented to have six degrees of freedom.

Meanwhile, since in some example embodiments, as illustrated on the lower side of FIG. 8, the surgical task is performed using the guide tube 212 that is flexible and has multiple degrees of freedom, the guide tube 212 and each of the tools (the first tool 214a and the second tool 214b), which are extended from the guide tube 212 and have distal ends on which the end effectors 218a and 218b are mounted, operate while interacting with each other, the guide tube 212 and the endoscope 216 extended from the guide tube 212 operate while interacting with each other, and operations of elements of the slave robot 200 can be controlled in an integrated manner using redundancy caused by a degree of freedom of a proximal part of the slave robot 200, i.e., the guide tube 212 and the mounting arm 202 to which the guide tube 212 is connected. Thus, an operation with six degrees of freedom can be performed by each of the tools 214a and 214b and the endoscope 216 implemented to have a degree of freedom that is less than six degrees of freedom (for example, four degrees of freedom).

Figure 9:
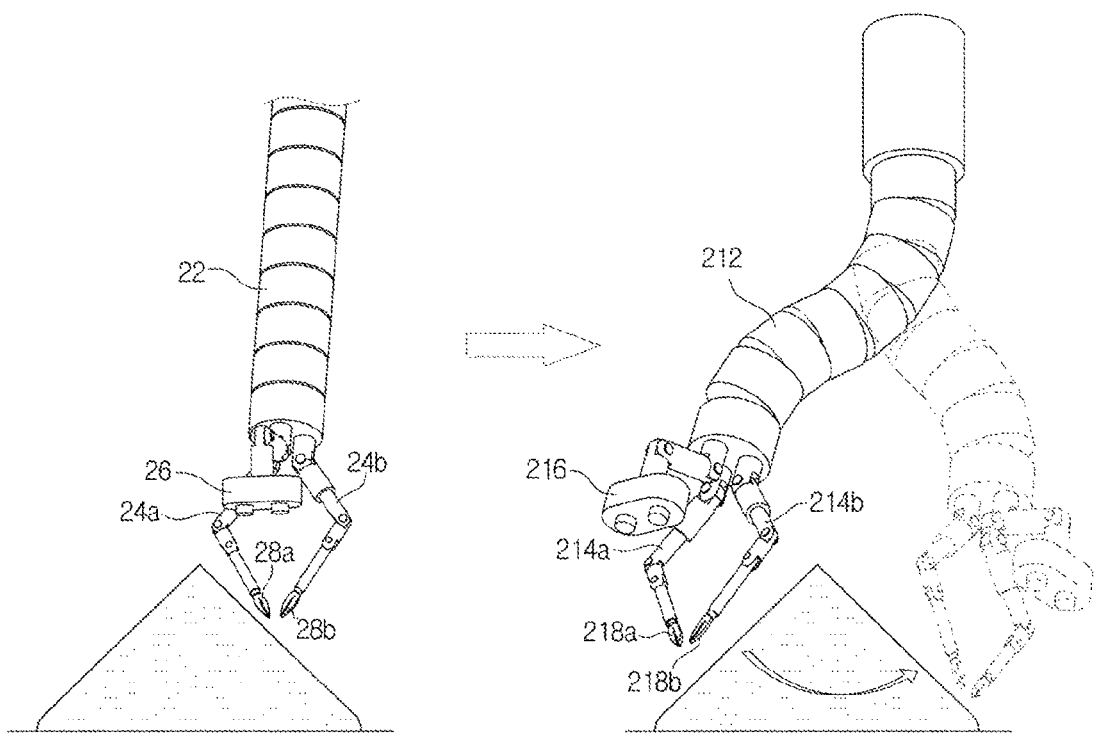
FIG. 9 is a conceptual view illustrating performance of a complex task achieved by some example embodiments.

FIG. 9 is a conceptual view illustrating performance of a complex task achieved by some example embodiments.

The left drawing of FIG. 9 illustrates a case that a surgical task is performed using an existing tool controlling method, and the right drawing of FIG. 9 illustrates a case that the surgical task is performed using a tool controlling method according to some example embodiments.

When the surgical task is performed using a rigid (inflexible) fixed type guide tube or a rod-shaped guide tube according to the related art or even when the surgical task is performed using the guide tube 22 that is flexible and has multiple degrees of freedom, as illustrated on the upper side of FIG. 8, the guide tube 22 and each of the tools (the first tool 24a and the second tool 24b), which are extended from the guide tube 22 and have distal ends on which the end effectors 28a and 28b are mounted, operate individually, and the guide tube 22 and the endoscope 26 extended from the guide tube 22 operate individually. Thus, the surgical task performed by each of the tools 24a and 24b is limited to a simple task (for example, passing and running).

Meanwhile, since in some example embodiments, as illustrated on the right side of FIG. 9, the surgical task is performed using the guide tube 212 that is flexible and has multiple degrees of freedom, the guide tube 212 and each of the tools (the first tool 214a and the second tool 214b), which are extended from the guide tube 212 and have distal ends on which the end effectors 218a and 218b are mounted, operate while interacting with each other, the guide tube 212 and the endoscope 216 extended from the guide tube 212 operate while interacting with each other, and operations of elements of the slave robot 200A can be controlled in an integrated manner using redundancy of the slave robot 200A. Thus, an extension in the workspace of the tool (see FIG. 5), minimization of rigidity required for each of joints of the tools (see FIG. 6), and minimization of a possibility of collision between each of the tools and the peripheral obstacle (see FIG. 7) can be achieved, and various individual objectives are combined with each other so that a complex task (for example, auto-suturing) that cannot be performed by the existing tool controlling method, can be performed.

When an objective function of the system for achieving the objective of the system to perform the complex task described with reference to FIG. 9 is w, the objective function w of the system may be defined as a weighted sum of a plurality of individual objective functions $w_1$, $w_2$, and $w_3$ described with reference to FIGS. 5 through 7 ($w=aw_1+bw_2+cw_3$). That is, the objective function w of the whole system may be represented as a weighted sum of the individual objective function $w_1$ defined as the distance between each of the tools 214a and 214b and the joint limit or the reciprocal number $1/d_1$ of the distance $d_1$ between the endoscope 216 and the joint limit, the individual objective function $w_2$ defined as the joint torque square sum ($\tau_1^2+\tau_2^2+\tau_3^2+\ldots$) of the torque squares ($\tau_1^2, \tau_2^2, \tau_3^2 \ldots$) of each of joints that constitute the plurality of tools 214a and 214b and the endoscope 216, and the individual objective function $w_3$ defined as the distance between each of the tools 214a and 214b and the peripheral obstacle or the reciprocal number $1/d_3$ of the distance $d_3$ between the endoscope 216 and the peripheral obstacle. In some example embodiments, the objective function w ($w=aw_1+bw_2+cw_3$) of the system varies according to a flow of time. That is, weights multiplied with individual objective functions vary depending on the type of a surgical task performed by the slave robot 200A. For example, when the surgical task performed by the slave robot 200A is cannulation, the individual objective to minimize a possibility of collision between the tool and the peripheral obstacle is more significant than the individual objective to enlarge a workspace of tools or to minimize rigidity required for each of joints of the tools. Thus, a weight c multiplied with the individual objective function $w_3$ for achieving the individual objective to minimize a possibility of collision between the tool and the peripheral obstacle is determined as a greater value than weights a and b multiplied with other individual objective functions $w_1$ and $w_2$.

Referring back to FIG. 4, elements of the redundancy inverse kinematics interpretation unit 142A will now be described in detail.

The Jacobian matrix calculation unit 144A calculates a Jacobian matrix J(q) multiplied with the speed vector q̇ of a joint from Equation 2, i.e., differential kinematics equation ṗ=J(q)q̇ that is obtained by differentiating Equation 1, i.e., p=f(q) that represents the relationship between the task variable p and the joint variable q, i.e., p=f(q) in relation to time. In some example embodiments, the Jacobian matrix calculation unit 144A calculates the Jacobian matrix J(q) of f(q) by inputting pieces of information (for example, information regarding lengths of links that connect between a joint and a joint) regarding a kinematics structure of the slave robot 200A to an algorithm for calculating the Jacobian matrix J(q).

The objective function calculation unit 145A calculates the objective function w shown in Equation 6, i.e., $$r = -k \frac{\partial w}{\partial q},$$

which represents an arbitrary vector r(q) shown in Equation 4, i.e., q̇=J#ṗ+($I_n$-J#J)r, which calculates a speed (speed vector q̇ of a joint) of each joint in the joint space using a pseudo inverse matrix J#(q) of the Jacobian matrix J(q) in the slave robot 200A having redundancy. The objective function w (the objective function of the whole system) may be represented as a weighted sum of a plurality of individual objective functions $w_1$ to $w_n$ ($w=aw_1+bw_2+cw_3+\ldots$). Examples of the individual objective functions $w_1$ to $w_n$ may include a reciprocal number of a distance between each of the tools 214a and 214b and a joint limit, a joint torque square sum that constitutes the plurality of tools 214a and 214b and the endoscope 216, and a reciprocal number of a distance between each of the tools 214a and 214b and a peripheral obstacle. In some example embodiments, the objective function w of the system varies depending on a flow of time. That is, the weights a, b, c, and . . . multiplied with the individual objective functions $w_1$ to $w_n$ vary depending on the type of the surgical task performed by the slave robot 200A. The objective function calculation unit 145A determines the weights a, b, c, and . . . multiplied with the individual objective functions $w_1$ to $w_n$ depending on the type of the surgical task performed by the slave robot 200A. The objective function calculation unit 145A predicts the type of the surgical task to be performed by the manipulator using information (position information and speed information of the master manipulation units 112L and 112R) regarding an operation of the master manipulation units 112L and 112R detected by the position/orientation detection unit 120A and the speed detection unit 125A and the result of learning of a plurality of operations of the surgical task that has been already stored in the storage unit 130A. In some example embodiments, the surgical task is one among suturing, passing, running, and cannulation, and the plurality of operations of the surgical task includes at least one of orient, push, and pull. Thus, the objective function calculation unit 145A determines the task of the surgical task performed by the slave robot 200A, determines the weights a, b, c, and . . . multiplied with the individual objective functions $w_1$ to $w_n$ based on the result of determination, and then calculates the objective function w of the system by multiplying each individual objective function by each determined weight.

The redundancy utilization unit 146A calculates a solution in the joint space in which the objective function w of the whole system is minimized, i.e., a desired rotational angle q of each of joints that constitute the mounting arm 202, the guide tube 212, the plurality of tools 214a and 214b, and the endoscope 216. The redundancy utilization unit 146A calculates a speed (speed vector q̇ of a joint) of each joint in the joint space in which the objective function w is minimized, by substituting the objective function w calculated by the objective function calculation unit 145A with the above Equation 6 and then by substituting Equation 6 with which the objective function w is substituted, with the above Equation 4. The redundancy utilization unit 146A calculates the desired rotational angle q of each of joints that constitute the mounting arm 202, the guide tube 212, the plurality of tools 214a and 214b, and the endoscope 216 that is the solution in the final joint space by integrating the calculated speed (speed vector q̇ of a joint) of each joint in the joint space.

The image processing unit 147A performs processing on an input image, whereby an image input by an image information obtaining unit 220A of the slave robot 200A, for example, the endoscope 216 and/or the ultrasonic probe (not shown) is output as a pictorial image. In some example embodiments, examples of image processing may include enlargement, reduction, movement, edition and filtering of a captured image.

The communication unit 150A that is a communication circuit that is connected to the main controller 140A and a communication unit 250A of the slave robot 200A via a wired/wireless communication network and transmits/receives data to/from the main controller 140A and the communication unit 250A of the slave robot 200A may transmit a control signal (desired rotational angle q of joints) generated by the redundancy utilization unit 146A to the slave robot 200A or may receive image information (endo scope image information and/or ultrasonic image information) obtained by the image information obtaining unit 220A from the slave robot 200A.

The display unit 116A outputs various reference images, such as a pictorial image corresponding to an endo scope image transmitted from the endoscope 216 of the slave robot 200A, a pictorial image corresponding to an ultrasonic image transmitted from the ultrasonic probe (not shown) of the slave robot 200A, an X-ray image that is captured before an operation is performed, a CT image, and an MRI image, as visual information.

The slave robot 200A operates the mounting arm 202, the guide tube 212, and the plurality of tools 214a, 214b, and endoscope 216 according to the control signal received from the master device 100A so as to perform a manipulation required for surgery directly on the patient. The slave robot 200A may include the image information obtaining unit 220A, a storage unit 230A, a slave controller 240A, the communication unit 250A, a servo controller 260A, and a driving unit 270A, as illustrated in FIG. 4.

The image information obtaining unit 220A is inserted into the patient's body, moves, captures an inside of internal organs or the body cavity, and obtains image information of the operating part. The image information obtaining unit 220A may be implemented with the endoscope 216 and the ultrasonic probe (not shown). The image information obtained by the image information obtaining unit 220A may be transmitted to an image processing unit 247A in the slave controller 240A, may undergo an image processing procedure or may be transmitted to the master device 100A through the communication unit 250A without the image processing procedure.

The storage unit 230A may store information and an algorithm required to control an operation of the slave robot 200A and information obtained by the slave robot 200A. For example, image information regarding the operating part obtained by the image information obtaining unit 220A is stored in the storage unit 230A.

The slave controller 240A that is a processor for connecting elements of the slave robot 200A and for controlling the operation of the slave robot 200A, may transmit the image information of the operating part obtained by the image information obtaining unit 220A to the master device 100A through the communication unit 250A or may receive the control signal (desired rotational angle of each joint) generated by the redundancy utilization unit 146A within the main controller 140A from the communication unit 250A and transmit the received control signal to the servo controller 260A. Also, the slave controller 240A may include the image processing unit 247A that performs processing on an image of the operating part obtained by the image information obtaining unit 220A. In some example embodiments, image processing may include enlargement, reduction, rotation, movement, edition, and/or filtering of a captured image. The image processing procedure performed within the slave controller 240A may be omitted as needed.

The communication unit 250A that is a communication circuit that is connected to the slave controller 240A and the communication unit 150A of the master device 100A via a wired/wireless communication network and transmits/receives data to/from the slave controller 240A and the communication unit 150A of the master device 100A may receive a control signal (desired rotational angle q of joints) generated by utilizing redundancy from the master device 100A or may transmit image information (endoscope image information and/or ultrasonic image information) obtained by the image information obtaining unit 220A to the master device 100A.

The servo controller 260A calculates a joint torque $\tau$ for tracking the desired rotational angle q of joints transmitted from the redundancy utilization unit 146A within the main controller 140A, generates a torque control signal corresponding to the calculated joint torque $\tau$, and outputs the generated torque control signal to the driving unit 270A that rotationally drives each of joints that constitute the mounting arm 202, the guide tube 212, each of the tools 214a and 214b, and the endoscope 216.

The driving unit 270A that is an actuator, such as a motor for transmitting power caused by electricity or hydraulic pressure to each of a plurality of joints that constitute the mounting arm 202, the guide tube 212, each of the tools 214a and 214b, and the endoscope 216, rotationally drives each of the joints that constitute the mounting arm 202, the guide tube 212, each of the tools 214a and 214b, and the endoscope 216 according to the torque control signal transmitted from the servo controller 260A. In the slave robot 200A including the mounting arm 202, the guide tube 212 connected to the mounting arm 202, two tools 214a and 214b extended from the guide tube 212 when the surgical task is performed, and one endoscope 216 illustrated in FIGS. 3A through 3C described above, a degree of freedom of the mounting arm 202, the guide tube 212, and each of the tools 214a and 214b in the joint space is 6 and a degree of freedom of the endoscope 216 in the joint space is 3 such that 27 rotational joints are disposed on the slave robot 200A. Thus, 27 actuators are required to drive the rotational joints.

Figure 10:
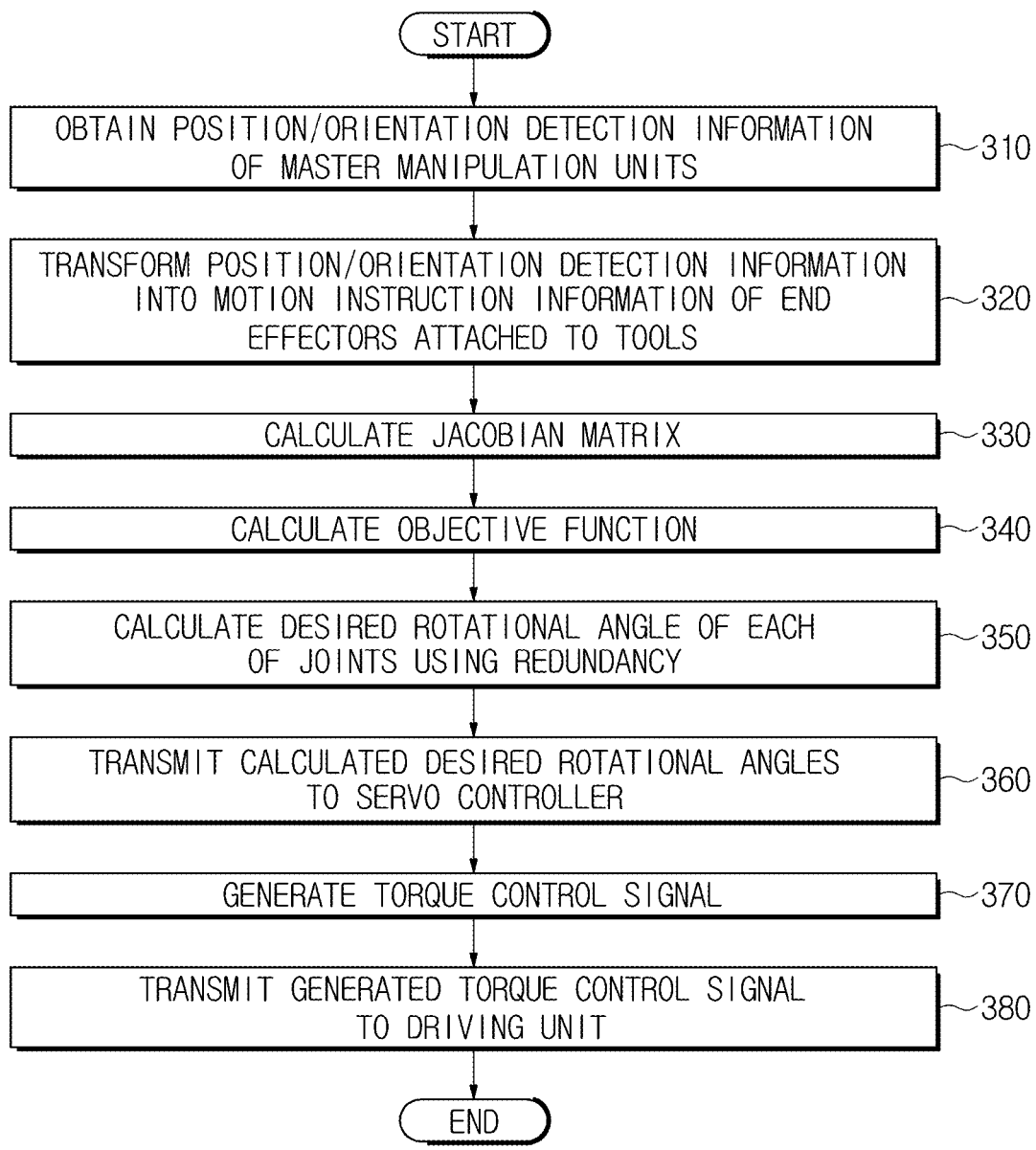
FIG. 10 is a flowchart illustrating a method of controlling a surgical robot in accordance with some example embodiments.

FIG. 10 is a flowchart illustrating a method of controlling a surgical robot in accordance with some example embodiments.

As an initial condition for describing an operation of some example embodiments, it is premised that the slave robot 200A has redundancy and each of the mounting arm 202, the guide tube 212, two tools 214a and 214b, and one endoscope 216 includes a plurality of links and a plurality of joints. Also, it is premised that the mounting arm 202 and the guide tube 212 operate while interacting with each other, the guide tube 212 and each of the tools 214a and 214b operate while interacting with each other, and the guide tube 212 and one endoscope 216 operate while interacting with each other. Also, it is premised that a scaling factor applied when motion scaling between an operation of the master manipulation units 112L and 112R of the master device 100A and an operation of a distal end (a plurality of tools and endoscope) of the slave robot 200A is performed, an algorithm required to calculate a Jacobian matrix, information regarding a kinematics structure of the slave robot 200A, a plurality of individual objective functions for achieving a plurality of individual objectives required to calculate an objective function, the result of learning regarding a plurality of operations that constitute a surgical task, and weights multiplied with individual objective functions depending on the type of the surgical task have been previously stored in the storage unit 130A.

First, if surgery starts and a manipulator (typically a doctor) of the master manipulation units 112L and 112R performs a desired operation (that may or may not be predetermined) using the master manipulation units 112L and 112R so as to perform the surgical task, the position/orientation detection unit 120A of the master device 100A detects position information x', y', and z' and orientation information $\alpha'$, $\beta'$, and $\gamma'$ of the master manipulation units 112L and 112R and transmits the detected position information x', y', and z' and the detected orientation information α', β', and γ' of the master manipulation units 112L and 112R to the main controller 140A (Operation 310).

Next, the transformation unit 141A within the main controller 140A transforms position and orientation information x', y', z', α', β', and γ' of the master manipulation units 112L and 112R obtained by the position/orientation detection unit 120A into motion instruction information in the task space of the slave robot 200A, i.e., the manipulator's desired position and orientation information x, y, z, α, β, and γ of the distal end (distal end of each of the plurality of tools and a distal end of the endoscope) of the slave robot 200A (Operation 320). In some example embodiments, the transformation unit 141A may calculate the motion instruction information x, y, z, α, β, and γ in the task space of the slave robot 200A by multiplying the position and orientation information x', y', z', α', β', and γ' of the master manipulation units 112L and 112R by the scaling factor applied when motion scaling between the operation of the master manipulation units 112L and 112R of the master device 100A and the operation of the distal end (a plurality of tools and endoscope) of the slave robot 200A is performed.

Subsequently, the Jacobian matrix calculation unit 144A within the redundancy inverse kinematics interpretation unit 142A of the main controller 140A calculates a Jacobian matrix $J(q)$ multiplied with the speed vector $\dot{q}$ of a joint from Equation 2, i.e., differential kinematics equation $\dot{p}=J(q)\dot{q}$ using the algorithm required to calculate a Jacobian matrix and pieces of information (for example, information regarding lengths of links that connect between a joint and a joint) regarding the kinematics structure of the slave robot 200A that have been already stored in the storage unit 130A (Operation 330).

Next, the objective function calculation unit 145A within the redundancy inverse kinematics interpretation unit 142A of the main controller 140A determines the type of the surgical task performed by the slave robot 200A, determines weights a, b, c, and . . . multiplied with individual objective functions based on the result of determination, and then calculates an objective function w of the whole system by multiplying each of the individual objective functions by each determined weight (Operation 340). In some example embodiments, the objective function calculation unit 145A may predict the type of the surgical task to be performed by the manipulator using information (position information and speed information of the master manipulation units 112L and 112R) regarding an operation of the master manipulation units 112L and 112R detected by the position/orientation detection unit 120A and the speed detection unit 125A and the result of learning of a plurality of operations of the surgical task that has been already stored in the storage unit 130A, may search the storage unit 130A for the weights a, b, c, and . . . multiplied with the individual objective functions according to the predicted surgical task (for example, cannulation), and then may calculate the objective function w of the system by multiplying each of the individual objective functions by each of the searched weights a, b, c, and . . . .

Subsequently, the redundancy utilization unit 146A within the redundancy inverse kinematics interpretation unit 142A of the main controller 140A calculates a desired rotational angle q of each of joints that constitute the mounting arm 202, the guide tube 212, a plurality of tools 214a and 214b, and the endoscope 216 using redundancy of the slave robot 200A (Operation 350). In some example embodiments, the redundancy utilization unit 146A calculates a speed (speed vector $\dot{q}$ of a joint) of each joint in the joint space in which the objective function w of the whole system calculated by the objective function calculation unit 145A is minimized and calculates a desired rotational angle q of each of joints that constitute the mounting arm 202, the guide tube 212, the plurality of tools 214a and 214b, and the endoscope 216 that is a solution in the final joint space by integrating the calculated speed (speed vector $\dot{q}$ of a joint) of each joint in the joint space.

Next, the main controller 140A transmits the desired rotational angle q of each of joints calculated by the redundancy utilization unit 146A to the slave controller 240A of the slave robot 200A through the communication unit 150A, and the slave controller 240A transmits the desired rotational angle q of each of joints transmitted from the main controller 140A to the servo controller 260A (Operation 360).

Subsequently, the servo controller 260A of the slave robot 200A calculates a joint torque τ for tracking the desired rotational angle q of each of joints transmitted from the redundancy utilization unit 146A within the main controller 140A and generates a torque control signal corresponding to the calculated joint torque τ (Operation 370).

Next, the servo controller 260A transmits the generated torque control signal to the driving unit 270A that rotationally drives each of joints that constitute the mounting arm 202, the guide tube 212, each of the tools 214a and 214b, and the endoscope 216 (Operation 380).

Through this procedure, various individual objectives (to enlarge a workspace of the tool, to minimize rigidity required for each joint of the tool, to minimize a possibility of collision between the tool and a peripheral obstacle, to minimize a degree of freedom required for the tool, and to perform a complex task) are achieved using redundancy of the slave robot 200A, and simultaneously, operations of elements (a mounting arm, a guide tube, a plurality of tools, and an endoscope) of the slave robot 200A can be controlled in an integrated manner.

The method of FIG. 10 may be used in more general purpose systems and/or for methods of controlling such systems. For example, the method may be used in aerospace robots and/or for controlling such robots so as to allow safe takeoff, movement, and/or landing of the robots.

Figure 11:
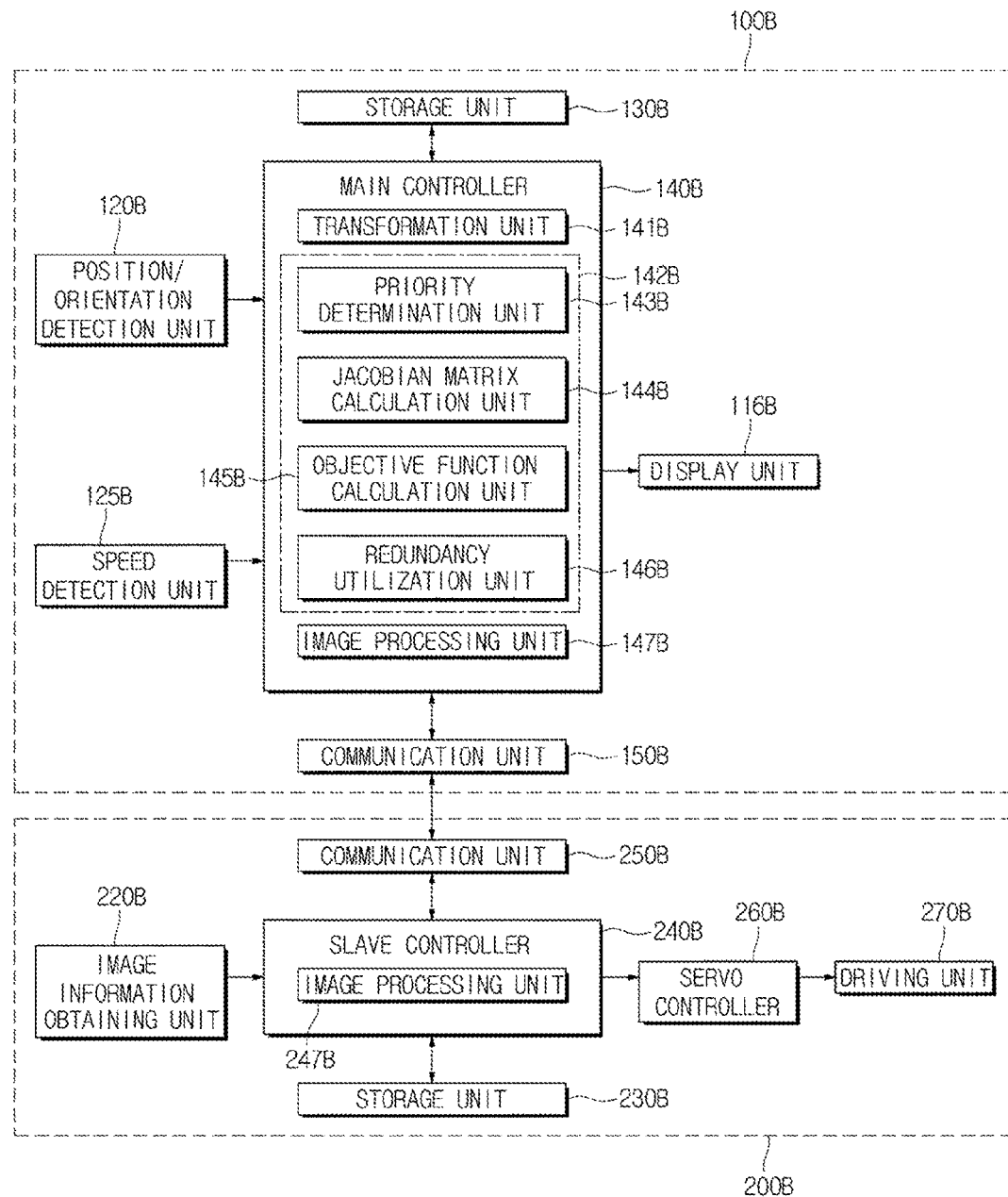
FIG. 11 is a control block diagram of a surgical robot in accordance with some example embodiments.

FIG. 11 is a control block diagram of a surgical robot in accordance with some example embodiments.

The surgical robot illustrated in FIG. 11 is different from the surgical robot illustrated in FIG. 4 in that a priority determination unit 143B is added to a redundancy inverse kinematics interpretation unit 142B of a main controller 140B of a master device 100B in comparison with the surgical robot of FIG. 4.

In some example embodiments, description of elements that use the same reference names and the same reference numerals as those of FIG. 4 will be omitted. (however, A and B marked after reference numerals are used to distinguish some example embodiments from each other.) A configuration of the priority determination unit 143B added to FIG. 11 and configurations of a storage unit 130B and a redundancy inverse kinematics interpretation unit 142B within the main controller 140B, functions of which vary due to the priority determination unit 143B will now be described.

The storage unit 130B of FIG. 11 is a memory in which information and an algorithm required to calculate a solution in the joint space, i.e., a desired rotational angle of each of joints that constitute a mounting arm 202, a guide tube 212, a plurality of tools 214a and 214b, and an endoscope 216 using redundancy of a slave robot 200B are stored. A scaling factor applied when motion scaling between an operation of master manipulation units 112L and 112R of the master device 100B and an operation of a distal end (a plurality of tools and endoscope) of the slave robot 200B is performed, priorities that are set to a task variable p, i.e., position/orientation information of the plurality of tools 214a and 214b and orientation information of the endoscope 216 (for example, a higher priority is set to the position/orientation information of the plurality of tools 214a and 214b between the position/orientation information of the plurality of tools 214a and 214b and the orientation information of the endoscope 216 or a higher priority is set to position information $x_1$, $y_1$, and $z_1$ of the distal end of the first tool 214a between the position information $x_1$, $y_1$, and $z_1$ and orientation information $\alpha_1$, $\beta_1$, and $\gamma_1$ of the distal end of the first tool 214a), an algorithm required to calculate a Jacobian matrix, information regarding a kinematics structure of the slave robot 200B, a plurality of individual objective functions for achieving a plurality of individual objectives required to calculate an objective function, the result of learning regarding a plurality of operations that constitute a surgical task, and weights multiplied with individual objective functions depending on the type of the surgical task are stored in the storage unit 130B.

Also, the storage unit 130B may store various reference images, such as an X-ray image captured before surgery is performed, a CT image, and an MRI image.

As illustrated in FIG. 11, the redundancy inverse kinematics interpretation unit 142B of the main controller 140B that is an element for generating a control signal (desired rotational angle of each of a plurality of joints that constitute each element) for controlling operations in an integrated manner of elements (mounting arm, guide tube, a plurality of tools, and endoscope) of the slave robot 200B using redundancy of the slave robot 200B includes the priority determination unit 143B, a Jacobian matrix calculation unit 144B, an objective function calculation unit 145B, and a redundancy utilization unit 146B.

Before describing the elements of the redundancy inverse kinematics interpretation unit 142B in detail, first, inverse kinematics interpretation when a priority is set to the task variable p in the slave robot 200B having redundancy will now be described.

When the system has redundancy, an inverse kinematics solution is calculated using a pseudo-inverse matrix $J^\#(q)$ of a Jacobian matrix $J(q)$, as described above.

In some example embodiments, when a priority is set to the task variable p, for example, when the task variable p is divided into $p_1$ and $p_2$ according to priorities and a higher priority is set to $p_1$, an Equation for calculating a speed (speed vector $\dot{q}$ of a joint) of each joint in the joint space using the pseudo-inverse matrix of the Jacobian matrix may be represented as the following Equation 7, and $\hat{J}_2$ shown in Equation 7 may be defined as the following Equation 8.

$$\dot{q}=J_1^\#\dot{p}_1+\hat{J}_2^\#(\dot{p}_2-J_2J_1^\#\dot{p}_1)+(I_n-J_1^\#J_1)(I_n-\hat{J}_2^\#\hat{J}_2)r \quad \text{[Equation 7]}$$

$$\hat{J}_2=J_2(I_n-J_1^\#J_1) \quad \text{[Equation 8]}$$

In some example embodiments, $p_1$ and $p_2$ are subvectors that are obtained by classifying the task variable p according to priorities, $J_1$ and $J_2$ are Jacobian matrices corresponding to $p_1$ and $p_2$, $I_n$ is an n×n unit matrix (identity matrix), and r is an arbitrary vector.

In description of a method of assigning a priority to the task variable p, for example, a higher priority may be set to position and orientation information of the plurality of tools 214a and 214b (when priorities between position/orientation information of different tools are different from each other) between the position and orientation information of the plurality of tools 214a and 214b and orientation information of the endoscope 216 (when the endoscope 216 has three degrees of rotational freedom in the roll, pitch, and yaw directions), or a higher priority may be set to position information $x_1$, $y_1$, and $z_1$ of the distal end of the first tool 214a between the position information $x_1$, $y_1$, and $z_1$ and orientation information $\alpha_1$, $\beta_1$, and $\gamma_1$ of the distal end of the first tool 214a (when priorities of position information and orientation information of one tool are different from each other).

Even when the task variable p is classified according to priorities, an arbitrary vector r(q) is defined and individual objective functions $w_1$ to $w_n$ and an objective function w of the whole system are defined so as to utilize redundancy, as shown in Equation 6 and as described above with reference to FIGS. 5 through 9, and thus detailed description thereof will be omitted.

Referring back to FIG. 11, elements of the redundancy inverse kinematics interpretation unit 142B will be described in detail.

The priority determination unit 143B classifies position and orientation information x, y, z, $\alpha$, $\beta$, and $\gamma$ of a distal end (each distal end of a plurality of tools and a distal end of an endoscope) of the slave robot 200B transformed by a transformation unit 141B according to desired priorities (that may or may not be predetermined). In some example embodiments, it is premised that the position and orientation information of the distal end of the slave robot 200B, i.e., the task variable p is classified into $p_1$ and $p_2$ according to priorities, wherein a priority set to $p_1$ is higher than a priority set to $p_2$. For example, when a higher priority is set to position and orientation information of the plurality of tools 214a and 214b between the position and orientation information of the plurality of tools 214a and 214b and orientation information of the endoscope 216 (when priorities between position/orientation information of different tools are different from each other), the priority determination unit 143B determines the position and orientation information of the plurality of tools 214a and 214b as $p_1$ and determines the orientation information of the endoscope 216 as $p_2$. Also, for example, when a higher priority is set to position information $x_1$, $y_1$, and $z_1$ of the distal end of the first tool 214a between the position information $x_1$, $y_1$, and $z_1$ and orientation information $\alpha_1$, $\beta_1$, and $\gamma_1$ of the distal end of the first tool 214a (when priorities of position information and orientation information of one tool are different from each other), the priority determination unit 143B determines the position information $x_1$, $y_1$, and $z_1$ of the distal end of the first tool 214a as $p_1$ and determines the orientation information $\alpha_1$, $\beta_1$, and $\gamma_1$ of the distal end of the first tool 214a as $p_2$.

The Jacobian matrix calculation unit 144B calculates a Jacobian matrix $J_1(q)$ corresponding to $p_1$ having a relatively high priority and a Jacobian matrix $J_2(q)$ corresponding to $p_2$ having a relatively low priority of the task variable p by inputting pieces of information (for example, information regarding lengths of links that connect between a joint and a joint) regarding a kinematics structure of the slave robot 200B to an algorithm for calculating a Jacobian matrix.

The objective function calculation unit 145B calculates an objective function w shown in Equation 6, i.e., $$r=-k\frac{\partial w}{\partial q},$$

which represents an arbitrary vector r(q) shown in Equation 7, i.e., $\dot{q}_1 = J_1^{\#}\dot{p}_1 + \hat{J}_2^{\#}(\dot{p}_2 - J_2 J_1^{\#}\dot{p}_1) + (I_n - J_1^{\#} J_1)(I_n - \hat{J}_2^{\#}\hat{J}_2)r$, which calculates a speed (speed vector $\dot{q}$ of a joint) of each joint in the joint space using a pseudo-inverse matrix $J_1^{\#}(q)$ of the Jacobian matrix $J_1(q)$ corresponding to $p_1$ having a relatively high priority of the task variable p and a pseudo-inverse matrix $J_2^{\#}(q)$ of the Jacobian matrix $J_2(q)$ corresponding to $p_2$ having a relatively low priority of the task variable p in the slave robot 200B having redundancy. The objective function w (objective function of the whole system) may be represented as a weighted sum of a plurality of individual objective functions $w_1$ to $w_n$ ($w = aw_1 + bw_2 + cw_3 + \ldots$). Examples of the individual objective functions may include a reciprocal number of a distance between each of the tools 214a and 214b and a joint limit, a joint torque square sum that constitutes the plurality of tools 214a and 214b and the endoscope 216, and a reciprocal number of a distance between each of the tools 214a and 214b and a peripheral obstacle. In some example embodiments, the objective function w of the whole system varies depending on a flow of time. That is, the weights a, b, c, and . . . multiplied with the individual objective functions $w_1$ to $w_n$ vary depending on the type of the surgical task performed by the slave robot 200B. The objective function calculation unit 145B determines the weights a, b, c, and . . . multiplied with the individual objective functions $w_1$ to $w_n$ varying depending on the type of the surgical task performed by the slave robot 200B. The objective function calculation unit 145B predicts the type of the surgical task to be performed by the manipulator using information (position information and speed information of the master manipulation units 112L and 112R) regarding an operation of the master manipulation units 112L and 112R detected by a position/orientation detection unit 120B and a speed detection unit 125B and the result of learning of a plurality of operations of the surgical task that has been previously stored in the storage unit 130B. In some example embodiments, the surgical task is one among suturing, passing, running, and cannulation, and the plurality of operations of the surgical task includes at least one of orient, push, and pull. Thus, the objective function calculation unit 145B determines the task of the surgical task performed by the slave robot 200B, determines the weights a, b, c, and . . . multiplied with the individual objective functions $w_1$ to $w_n$ based on the result of determination, and then calculates the objective function w of the whole system by multiplying each individual objective function by each determined weight.

The redundancy utilization unit 146B calculates a solution in the joint space in which the objective function w of the whole system is minimized, i.e., a desired rotational angle q of each of joints that constitute the mounting arm 202, the guide tube 212, the plurality of tools 214a and 214b, and the endoscope 216. The redundancy utilization unit 146B calculates a speed (speed vector $\dot{q}$ of a joint) of each joint in the joint space in which the objective function w is minimized, by substituting the objective function w calculated by the objective function calculation unit 145B with the above Equation 6 and then by substituting Equation 6 with which the objective function w is substituted, with the above Equation 7. The redundancy utilization unit 146B calculates the desired rotational angle q of each of joints that constitute the mounting arm 202, the guide tube 212, the plurality of tools 214a and 214b, and the endoscope 216 that is the solution in the final joint space by integrating the calculated speed (speed vector $\dot{q}$ of a joint) of each joint in the joint space.

Figure 12:
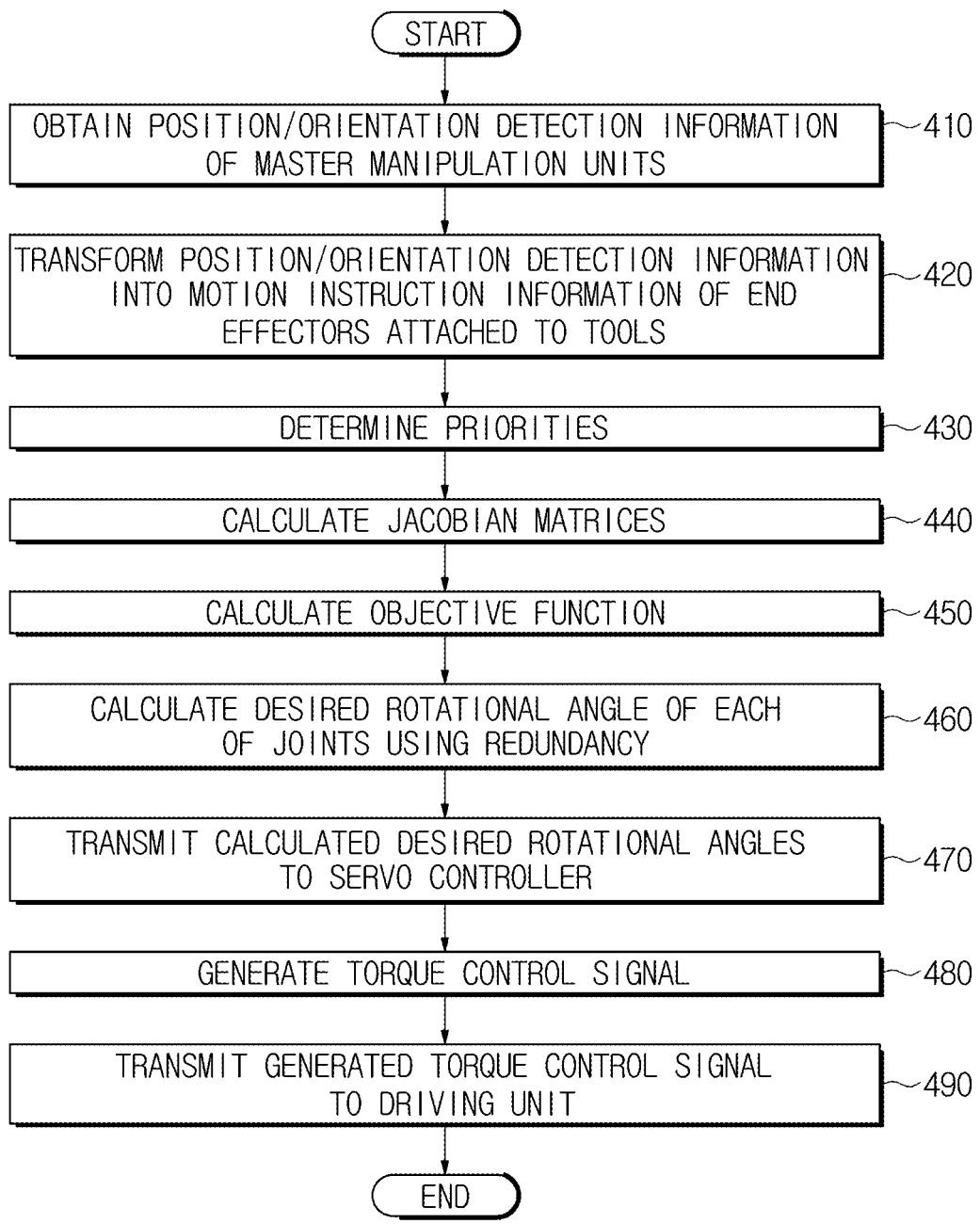
FIG. 12 is a flowchart illustrating a method of controlling a surgical robot in accordance with some example embodiments.

FIG. 12 is a flowchart illustrating a method of controlling a surgical robot in accordance with some example embodiments.

As an initial condition for describing an operation of some example embodiments, it is premised that the slave robot 200B has redundancy and each of the mounting arm 202, the guide tube 212, two tools 214a and 214b, and one endoscope 216 includes a plurality of links and a plurality of joints. Also, it is premised that the mounting arm 202 and the guide tube 212 operate while interacting with each other, the guide tube 212 and each of the tools 214a and 214b operate while interacting with each other, and the guide tube 212 and one endoscope 216 operate while interacting with each other. Also, it is premised that a scaling factor applied when motion scaling between an operation of the master manipulation units 112L and 112R of the master device 100B and an operation of a distal end (a plurality of tools and endoscope) of the slave robot 200B is performed, priorities that are set to the task variable p, i.e., position/orientation information of the plurality of tools 214a and 214b and orientation information of the endoscope 216, an algorithm required to calculate a Jacobian matrix, information regarding a kinematics structure of the slave robot 200B, a plurality of individual objective functions for achieving a plurality of individual objectives required to calculate an objective function, the result of learning regarding a plurality of operations that constitute a surgical task, and weights multiplied with individual objective functions depending on the type of the surgical task have been previously stored in the storage unit 130B.

First, if surgery starts and a manipulator (typically a doctor) of the master manipulation units 112L and 112R performs a desired operation (that may or may not be predetermined) using the master manipulation units 112L and 112R so as to perform the surgical task, the position/orientation detection unit 120B of the master device 100B detects position information x', y', and z' and orientation information α', β', and γ' of the master manipulation units 112L and 112R and transmits the detected position information x', y', and z' and the detected orientation information α', β', and γ' of the master manipulation units 112L and 112R to the main controller 140B (Operation 410).

Next, the transformation unit 141B within the main controller 140B transforms position and orientation information x', y', z', α', β', and γ' of the master manipulation units 112L and 112R obtained by the position/orientation detection unit 120B into motion instruction information in the task space of the slave robot 200B, i.e., the manipulator's desired position and orientation information x, y, z, α, β, and γ of the distal end (distal end of each of the plurality of tools and a distal end of the endoscope) of the slave robot 200B (Operation 420). In some example embodiments, the transformation unit 141B may calculate the motion instruction information x, y, z, α, β, and γ in the task space of the slave robot 200B by multiplying the position and orientation information x', y', z', α', β', and γ' of the master manipulation units 112L and 112R by the scaling factor applied when motion scaling between the operation of the master manipulation units 112L and 112R of the master device 100B and the operation of the distal end (a plurality of tools and endoscope) of the slave robot 200B is performed.

Subsequently, the priority determination unit 143B within the redundancy inverse kinematics interpretation unit 142B of the main controller 140B classifies position and orientation information x, y, z, α, β, and γ of the distal end (each distal end of a plurality of tools and a distal end of an endoscope) of the slave robot 200B transformed by the transformation unit 141B, i.e., the task variable p according to desired priorities (that may or may not be predetermined) (Operation 430). When it is premised that the task variable p is classified into $p_1$ and $p_2$ according to priorities, wherein a priority set to $p_1$ is higher than a priority set to $p_2$, for example, when a higher priority is set to position and orientation information of the plurality of tools 214a and 214b between the position and orientation information of the plurality of tools 214a and 214b and orientation information of the endoscope 216, the priority determination unit 143B determines the position and orientation information of the plurality of tools 214a and 214b as $p_1$ and determines the orientation information of the endoscope 216 as $p_2$.

Next, the Jacobian matrix calculation unit 144B within the redundancy inverse kinematics interpretation unit 142B of the main controller 140B calculates a Jacobian matrix $J_1(q)$ corresponding to $p_1$ having a relatively high priority of the task variable p and a Jacobian matrix $J_2(q)$ corresponding to $p_2$ having a relatively low priority of the task variable p using the algorithm required to calculate a Jacobian matrix and pieces of information (for example, information regarding lengths of links that connect between a joint and a joint) regarding the kinematics structure of the slave robot 200B that have been already stored in the storage unit 130B (Operation 440).

Next, the objective function calculation unit 145B within the redundancy inverse kinematics interpretation unit 142B of the main controller 140B determines the type of the surgical task performed by the slave robot 200B, determines weights a, b, c, and . . . multiplied with individual objective functions based on the result of determination, and then calculates an objective function w of the whole system by multiplying each of the individual objective functions by each determined weight (Operation 450). In some example embodiments, the objective function calculation unit 145B may predict the type of the surgical task to be performed by the manipulator, i.e., the type of the surgical task performed by the slave robot 200B using information (position information and speed information of the master manipulation units 112L and 112R) regarding an operation of the master manipulation units 112L and 112R detected by the position/orientation detection unit 120B and the speed detection unit 125B and the result of learning of a plurality of operations of the surgical task that has been already stored in the storage unit 130B, may search the storage unit 130B for the weights a, b, c, and . . . multiplied with the individual objective functions according to the predicted surgical task (for example, cannulation), and then may calculate the objective function w of the whole system by multiplying each of the individual objective functions by each of the searched weights a, b, c, and . . . .

Subsequently, the redundancy utilization unit 146B within the redundancy inverse kinematics interpretation unit 142B of the main controller 140B calculates a desired rotational angle q of each of joints that constitute the mounting arm 202, the guide tube 212, a plurality of tools 214a and 214b, and the endoscope 216 using redundancy of the slave robot 200B (Operation 460). In some example embodiments, the redundancy utilization unit 146B calculates a speed (speed vector q̇ of a joint) of each joint in the joint space in which the objective function w of the whole system calculated by the objective function calculation unit 145B is minimized and calculates a desired rotational angle q of each of joints that constitute the mounting arm 202, the guide tube 212, the plurality of tools 214a and 214b, and the endoscope 216 that is a solution in the final joint space by integrating the calculated speed (speed vector q̇ of a joint) of each joint in the joint space.

Next, the main controller 140B transmits the desired rotational angle q of each of joints calculated by the redundancy utilization unit 146B to a slave controller 240B of the slave robot 200B through a communication unit 150B, and the slave controller 240B transmits the desired rotational angle q of each of joints transmitted from the main controller 140B to a servo controller 260B (Operation 470).

Subsequently, the servo controller 260B of the slave robot 200B calculates a joint torque τ for tracking the desired rotational angle q of each of joints transmitted from the redundancy utilization unit 146B within the main controller 140B and generates a torque control signal corresponding to the calculated joint torque τ (Operation 480).

Next, the servo controller 260B transmits the generated torque control signal to a driving unit 270B that rotationally drives each of joints that constitute the mounting arm 202, the guide tube 212, each of the tools 214a and 214b, and the endoscope 216 (Operation 490).

As shown in FIG. 11, master device 100B also may include display unit 116B and image processing unit 147B.

As shown in FIG. 11, slave robot 200B also may include image information obtaining unit 220B, storage unit 230B, image processing unit 247B, and communication unit 250B.

Through this procedure, various individual objectives (to enlarge a workspace of the tool, to minimize rigidity required for each joint of the tool, to minimize a possibility of collision between the tool and a peripheral obstacle, to minimize a degree of freedom required for the tool, and to perform a complex task) are achieved using redundancy of the slave robot 200B, and simultaneously, operations of elements (a mounting arm, a guide tube, a plurality of tools, and an endoscope) of the slave robot 200B can be controlled in an integrated manner.

The method of FIG. 12 may be used in more general purpose systems and/or for methods of controlling such systems. For example, the method may be used in robots for handling hazardous materials and/or for controlling such robots so as to allow safe movement, packaging, and/or shipment of hazardous materials.

Figure 13:
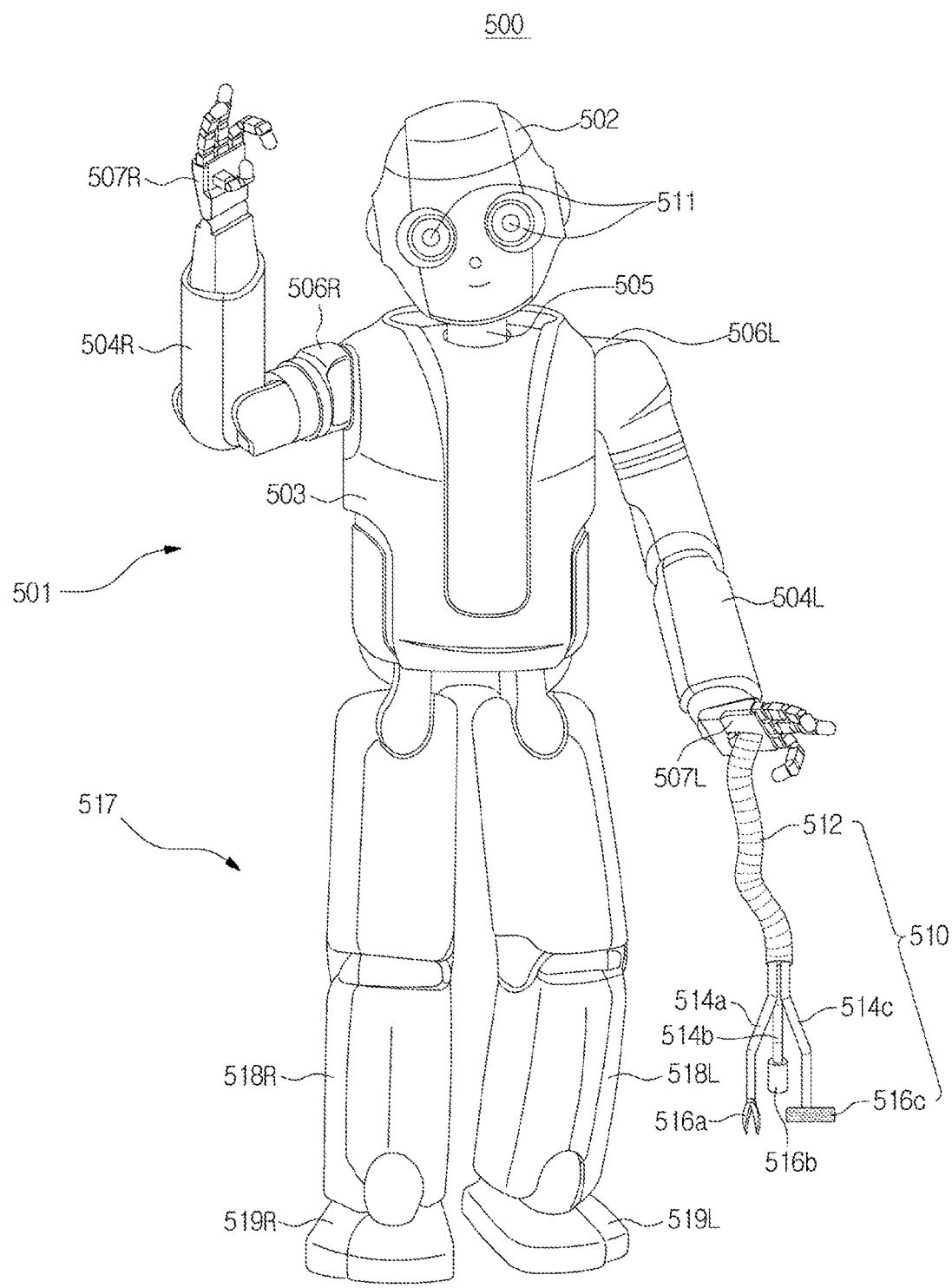
FIG. 13 is an exterior configuration view of a humanoid robot.

FIG. 13 is an exterior configuration view of a humanoid robot.

As illustrated in FIG. 13, a humanoid robot 500 that is a two-foot walking robot that moves upright using two legs 518L and 518R like a human being, includes an upper body 501 including a head 502, a body 503, and arms 504L and 504R and a lower body 517 including the two legs 518L and 518R.

The upper body 501 of the humanoid robot 500 includes the body 503, the head 502 connected to an upper part of the body 503 via a neck 505, two arms 504L and 504R connected to both sides of the upper part of the body 503 via shoulders 506L and 506R, and hands 507L and 507R connected to distal ends of two arms 504L and 504R. A camera 511 is mounted in each of mechanism units having a human eyes' shape on the head 502 so as to capture an image of a periphery of a movement space.

Two arms 504L and 504R may be implemented to be driven with multiple degrees of freedom. Two arms 504L and 504R include a plurality of links and a plurality of joints. In particular, as illustrated in FIG. 13, a multi-tool module 510 including a guide tube 512 and a plurality of tools 514a, 514b, and 514c having end effectors 516a, 516b, and 516c and extended from the guide tube 512 is connected to a distal end of a left arm 504L, i.e., a left hand 507L, as illustrated in FIG. 13. In some example embodiments, the multi-tool module 510 may be associated with right arm 504R. In some example embodiments, a first multi-tool module 510 may be associated with left arm 504L and a second multi-tool module 510 may be associated with right arm 504R.

When the humanoid robot 500 performs no task, the plurality of tools 514a, 514b, and 514c are embedded in the guide tube 512, and when the humanoid robot 500 performs a task, as illustrated in FIG. 13, the plurality of tools 514a, 514b, and 514c embedded in the guide tube 512 go out of the guide tube 512 and performs a task (for example, a cleaning task) according to a user's instruction. Hereinafter, the left arm 504L to which the multi-tool module 510 including the guide tube 512 and the plurality of tools 514a, 514b, and 514c is connected, is referred to as a mounting arm 504L, in particular.

In some example embodiments, the guide tube 512 and the plurality of tools 514a, 514b, and 514c may also include a plurality of links and a plurality of joints and may also be implemented to be driven with multiple degrees of freedom, like in the mounting arm 504L. In FIG. 13, cleaning equipment for performing the cleaning task, such as tongs for picking up a waste, a dust collector that collects dust in the air, and a cleaning cloth that cleans a dirty place, i.e., end effectors 516a, 516b, and 516c are mounted on distal ends of the plurality of tools 514a, 514b, and 514c.

The lower body 517 of the humanoid robot 500 includes two legs 518L and 518R connected to both sides of a lower part of the body 503 of the upper body 501 and feet 519L and 519R connected to distal ends of two legs 518L and 518R.

"R" and "L" in reference numerals represent right and left of the humanoid robot 500.

Figure 14:
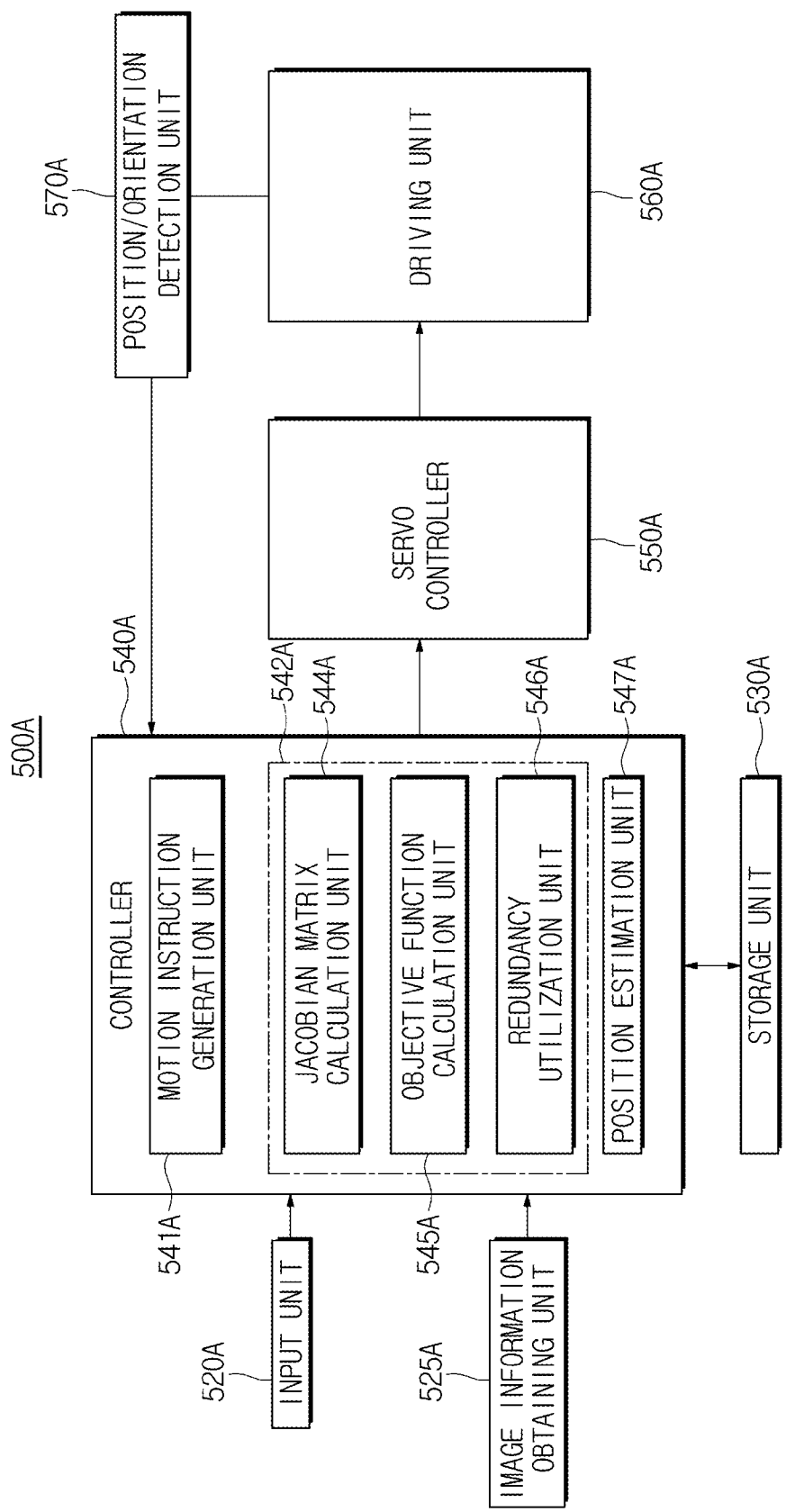
FIG. 14 is a control block diagram of a humanoid robot in accordance with some example embodiments.

FIG. 14 is a control block diagram of a humanoid robot in accordance with some example embodiments.

First, in some example embodiments, it is premised that each of a mounting arm 504L, a guide tube 512, and a plurality of tools 514a, 514b, and 514c that constitute a left arm of a humanoid robot 500 includes a plurality of links and a plurality of joints. Also, in some example embodiments, it is premised that the mounting arm 504L and the guide tube 512 operate while interacting with each other and the guide tube 512 and the tools 514a, 514b, and 514c operate while interacting with each other. Furthermore, in some example embodiments, it is premised that a humanoid robot 500A has redundancy, i.e., that a degree of freedom N in a joint space of the humanoid robot 500A is greater than a degree of freedom M in a task space of the humanoid robot 500A (N>M).

As illustrated in FIG. 14, the humanoid robot 500A may include an input unit 520A, an image information obtaining unit 525A, a storage unit 530A, a controller 540A, a servo controller 550A, a driving unit 560A, and a position/orientation detection unit 570A.

The input unit 520A is used for a user to input an operation instruction (for example, a walking instruction or a task instruction) of the humanoid robot 500A and may include a user interface (UI) or a remote controller.

The image information obtaining unit 525A detects light reflected from a subject, transforms the light into a digital signal, thereby obtaining an image of the periphery of the movement space. To this end, the image information obtaining unit 525A includes a camera 511 that captures the image of the periphery of the movement space and an image processing module that generates a two-dimensional (2D) image and 3D distance information by receiving an output of the camera 511. A charge-coupled device (CCD) camera, a complementary metal oxide semiconductor (CMOS) camera, or a time of flight (TOF) camera may be used as the camera 511. In addition, any device that may obtain image information regarding an object placed on a path on which the humanoid robot 500A walks may be used as the camera 511.

The storage unit 530A is a memory in which information and an algorithm required to calculate a solution in the joint space, i.e., a desired rotational angle of each of joints that constitute the mounting arm 504L, the guide tube 512, the plurality of tools 514a, 514b, and 514c using redundancy of the humanoid robot 500A are stored. An algorithm required to calculate a Jacobian matrix, information regarding a kinematics structure of the humanoid robot 500A, a plurality of individual objective functions for achieving a plurality of individual objectives required to calculate an objective function, and weights multiplied with individual objective functions depending on the type of the surgical task are stored in the storage unit 530A.

Also, the storage unit 530A may store the result of recognizing a position of the humanoid robot 500A and a map of the movement space that is drawn using a simultaneous localization and mapping (SLAM) algorithm.

The controller 540A that is a processor for controlling an overall operation of the humanoid robot 500A includes a motion instruction generation unit 541A, a redundancy inverse kinematics interpretation unit 542A, and a position estimation unit 547A.

The motion instruction generation unit 541A generates motion instructions x, y, z, $\alpha$, $\beta$, and $\gamma$ in the task space of the plurality of tools 514a, 514b, and 514c based on a user instruction signal transmitted from the input unit 520A, an image signal of the periphery of the movement space transmitted from the image information obtaining unit 525A, and position and orientation information of distal ends of the plurality of tools 514a, 514b, and 514c in the 3D space transmitted from the position/orientation detection unit 570A. In some example embodiments, the motion instructions x, y, z, $\alpha$, $\beta$, and $\gamma$ in the task space generated by the motion instruction generation unit 541A are the task variable p described above.

In some example embodiments, in order to perform position/orientation feedback control, the position and orientation information of distal ends of the plurality of tools 514a, 514b, and 514c in the 3D space transmitted from the position/orientation detection unit 570A are reflected when the motion instructions x, y, z, $\alpha$, $\beta$, and $\gamma$ in the task space are generated. However, when open-loop control is performed, the position and orientation information of distal ends of the plurality of tools 514a, 514b, and 514c in the 3D space are not reflected but motion instructions x, y, z, $\alpha$, $\beta$, and $\gamma$ in the task space for the plurality of tools 514a, 514b, and 514c are generated based on the user instruction signal transmitted from the input unit 520A and the image signal of the periphery of the movement space transmitted from the image information obtaining unit 525A.

The redundancy inverse kinematics interpretation unit 542A that is an element for generating a control signal (desired rotational angle of each of a plurality of joints that constitute each element) for controlling operations in an integrated manner of elements (mounting arm, guide tube, and a plurality of tools) of the humanoid robot 500A using redundancy of the humanoid robot 500A includes a Jacobian matrix calculation unit 544A, an objective function calculation unit 545A, and a redundancy utilization unit 546A.

The Jacobian matrix calculation unit 544A calculates a Jacobian matrix J(q) multiplied with a speed vector q̇ of a joint from Equation 2, i.e., differential kinematics equation ṗ=J(q)q̇ that is obtained by differentiating Equation 1, i.e., p=f(q) that represents the relationship between the task variable p and a joint variable q, i.e., p=f(q) in relation to time. In some example embodiments, the Jacobian matrix calculation unit 544A calculates the Jacobian matrix J(q) of f(q) by inputting pieces of information (for example, information regarding lengths of links that connect between a joint and a joint) regarding a kinematics structure of the humanoid robot 500A to an algorithm for calculating the Jacobian matrix J(q).

The objective function calculation unit 545A calculates the objective function w shown in Equation 6, i.e., $$r = -k\frac{\partial w}{\partial q},$$

which represents an arbitrary vector r(q) shown in Equation 4, i.e., q̇=J#ṗ+(I$_n$-J#J)r, which calculates a speed (speed vector q̇ of a joint) of each joint in the joint space using a pseudo inverse matrix J#(q) of the Jacobian matrix J(q) in the humanoid robot 500A having redundancy. The objective function w (weighted sum of individual objective functions of the whole system) may be represented as a weighted sum of a plurality of individual objective functions $w_1$ to $w_n$ (w=a$w_1$+b$w_2$+c$w_3$+ . . . ). Examples of the individual objective functions $w_1$ to $w_n$ may include a reciprocal number of a distance between each of the tools 514a, 514b, and 514c and a joint limit, a joint torque square sum that constitutes the plurality of tools 514a, 514b, and 514c, and a reciprocal number of a distance between each of the tools 514a, 514b, and 514c and a peripheral obstacle. In some example embodiments, the objective function w of the whole system varies depending on a flow of time. That is, the weights a, b, c, and . . . multiplied with the individual objective functions $w_1$ to $w_n$ vary depending on the type of the surgical task performed by the humanoid robot 500A. The objective function calculation unit 545A determines the type of the surgical task performed by the humanoid robot 500A, determines the weights a, b, c, and . . . multiplied with the individual objective functions $w_1$ to $w_n$ based on the result of determination, and then calculates the objective function w of the whole system by multiplying each of the individual objective functions by each determined weight.

The redundancy utilization unit 546A calculates a solution in the joint space in which the objective function w of the whole system is minimized, i.e., a desired rotational angle q of each of joints that constitute the mounting arm 504L, the guide tube 512, and the plurality of tools 514a, 514b, and 514c. The redundancy utilization unit 546A calculates a speed (speed vector q̇ of a joint) of each joint in the joint space in which the objective function w is minimized, by substituting the objective function w calculated by the objective function calculation unit 545A with the above Equation 6 and then by substituting Equation 6 with which the objective function w is substituted, with the above Equation 4. The redundancy utilization unit 546A calculates the desired rotational angle q of each of joints that constitute the mounting arm 504L, the guide tube 512, and the plurality of tools 514a, 514b, and 514c that is the solution in the final joint space by integrating the calculated speed (speed vector q̇ of a joint) of each joint in the joint space.

The position estimation unit 547A estimates the position of the humanoid robot 500A by applying the SLAM algorithm to odometry information calculated based on the image information obtained by the image information obtaining unit 525A, kinematics information (length information) of links that constitute the humanoid robot 500A, and rotational angle information of each rotational joint, and simultaneously draws a map corresponding to the movement space. In the SLAM algorithm, a position of a feature and position information and orientation information of the humanoid robot 500A are set as one state variable and are simultaneously estimated using a stochastic filter technique. A procedure thereof includes prediction, data association, and update operations, which are repeatedly performed. In some example embodiments, an extended Kalman filter or a particle filter may be used as the stochastic filter.

The servo controller 550A calculates a joint torque τ for tracking the desired rotational angle q of joints transmitted from the redundancy utilization unit 546A within the controller 540A, generates a torque control signal corresponding to the calculated joint torque τ, and outputs the generated torque control signal to the driving unit 560A that rotationally drives each of joints that constitute the mounting arm 504L, the guide tube 512, and each of the tools 514a, 514b, and 514c.

The driving unit 560A that is an actuator, such as a motor for transmitting power caused by electricity or hydraulic pressure to each of a plurality of joints that constitute the mounting arm 504L, the guide tube 512, and each of the tools 514a, 514b, and 514c, rotationally drives each of the joints that constitute the mounting arm 504L, the guide tube 512, and each of the tools 514a, 514b, and 514c according to the torque control signal transmitted from the servo controller 550A. When a degree of freedom of each of the mounting arm 504L, the guide tube 512, and the tools 514a, 514b, and 514c in the joint space is 6, 30 rotational joints are disposed on the left arm of the humanoid robot 500A. Thus, 30 actuators are required to drive the rotational joints.

The position/orientation detection unit 570A detects position and orientation of a distal end (each distal end of the plurality of tools) of the humanoid robot 500A. The position/orientation detection unit 570A includes a rotational angle sensor (not shown) that is mounted on each of a plurality of joints that constitute the plurality of tools 514a, 514b, and 514c and an arithmetic operation module that calculates position and orientation information of each distal end of the plurality of tools 514a, 514b, and 514c in the 3D space by substituting a rotational angle of each joint detected by the rotational angle sensor by an equation of forward kinematics of the plurality of tools 514a, 514b and 514c. The rotational angle sensor may be an encoder or a potentiometer. In some example embodiments, the position/orientation detection unit 570A including the rotational angle sensor and the arithmetic operation module has been described. However, any device that may detect information regarding position and orientation of each distal end of the plurality of tools 514a, 514b, and 514c may be used as the position/orientation detection unit 570A.

Figure 15:
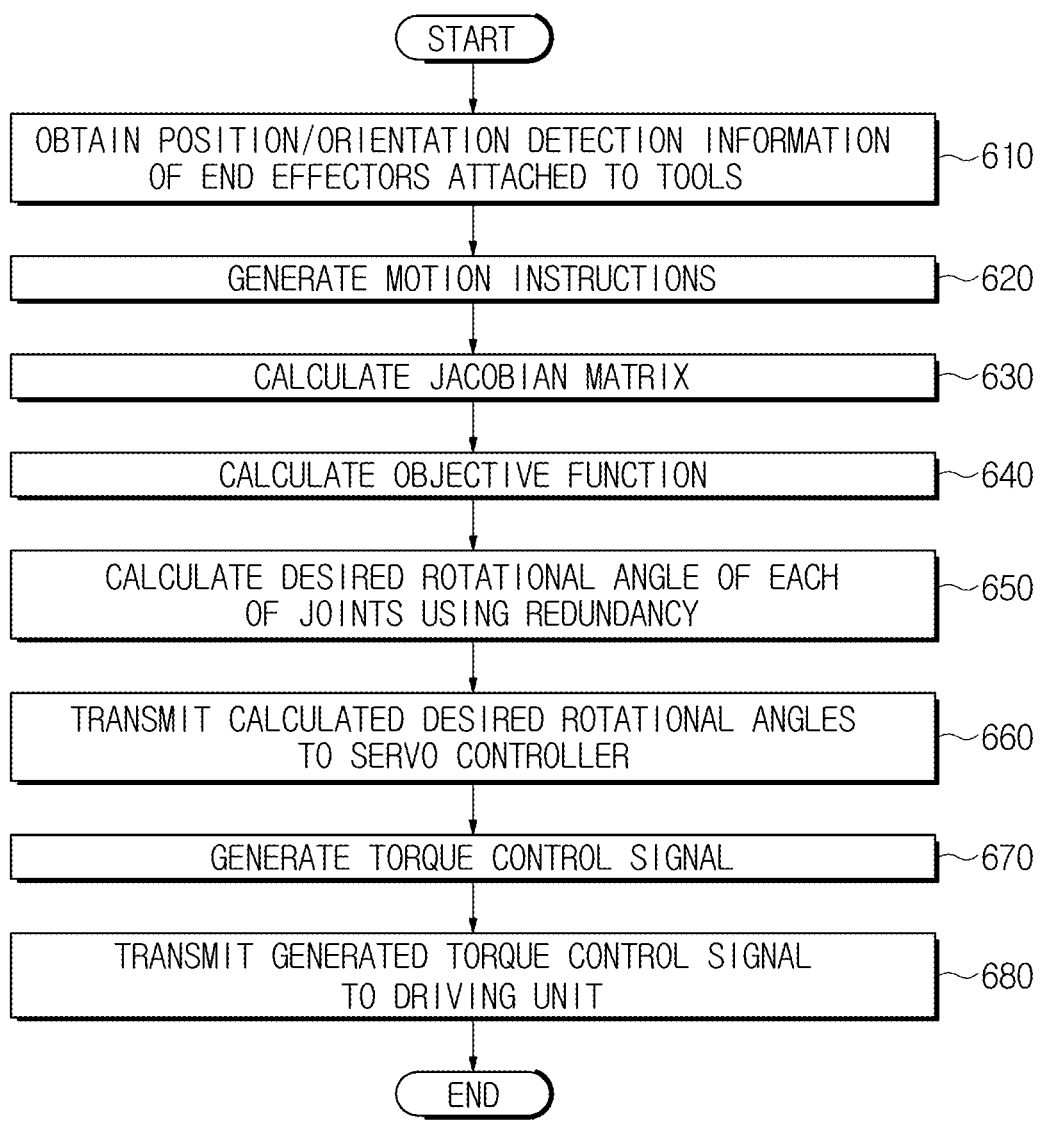
FIG. 15 is a flowchart illustrating a method of controlling a humanoid robot in accordance with some example embodiments.

FIG. 15 is a flowchart illustrating a method of controlling a humanoid robot in accordance with some example embodiments.

As an initial condition for describing an operation of some example embodiments, it is premised that the humanoid robot 500A, in particular, the left arm of the humanoid robot 500A illustrated in FIG. 13 has redundancy and each of the mounting arm 504L, the guide tube 512, and three tools 514a, 514b, and 514c includes a plurality of links and a plurality of joints. Also, it is premised that the mounting arm 504L and the guide tube 512 operate while interacting with each other and the guide tube 512 and each of the tools 514a, 514b, and 514c operate while interacting with each other.

Also, it is premised that an algorithm required to calculate a Jacobian matrix, information regarding a kinematics structure of the humanoid robot 500A, a plurality of individual objective functions for achieving a plurality of individual objectives required to calculate an objective function, and weights multiplied with individual objective functions depending on the type of the surgical task have been already stored in the storage unit 530A.

If a task instruction (for example, a cleaning instruction) of the humanoid robot 500A is input by the user through the input unit 520A, a task of the humanoid robot 500A starts.

First, if the task of the humanoid robot 500A starts, the controller 540A periodically receives position and orientation information of each distal end of the plurality of tools 514a, 514b, and 514c in the 3D space from the position/orientation detection unit 570A and performs the task (Operation 610).

Next, the motion instruction generation unit 541A within the controller 540A generates motion instructions x, y, z, α, β, and γ in the task space of the plurality of tools 514a, 514b, and 514c based on a user instruction signal transmitted from the input unit 520A, an image signal of the periphery of the movement space transmitted from the image information obtaining unit 525A, and position and orientation information of distal ends of the plurality of tools 514a, 514b, and 514c in the 3D space transmitted from the position/orientation detection unit 570A (Operation 620). In some example embodiments, the motion instructions x, y, z, α, β, and γ in the task space generated by the motion instruction generation unit 541A are a task variable p.

Subsequently, the Jacobian matrix calculation unit 544A within the redundancy inverse kinematics interpretation unit 542A of the controller 540A calculates a Jacobian matrix J(q) multiplied with a speed vector $\dot{q}$ of a joint from the above Equation 2, i.e., differential kinematics equation $\dot{p}=J(q)\dot{q}$ using the algorithm for calculating the Jacobian matrix and pieces of information (for example, information regarding lengths of links that connect between a joint and a joint) regarding a kinematics structure of the humanoid robot 500A that have been already stored in the storage unit 530A (Operation 630).

Next, the objective function calculation unit 545A within the redundancy inverse kinematics interpretation unit 542A of the controller 540A determines the type of the task performed by the humanoid robot 500A, determines weights a, b, c, and . . . based on the result of determination, and then calculates an objective function w of the whole system by multiplying each of individual objective functions by each determined weight (Operation 640).

Subsequently, the redundancy utilization unit 546A within the redundancy inverse kinematics interpretation unit 542A of the controller 540A calculates a desired rotational angle q of each of joints that constitute the mounting arm 504L, the guide tube 512, and the plurality of tools 514a, 514b, and 514c using redundancy of the humanoid robot 500A (Operation 650). In some example embodiments, the redundancy utilization unit 546A calculates a speed (speed vector $\dot{q}$ of a joint) of each joint in the joint space in which the objective function w of the whole system calculated by the objective function calculation unit 545A is minimized, and calculates the desired rotational angle q of each of joints that constitute the mounting arm 504L, the guide tube 512, and the plurality of tools 514a, 514b, and 514c that is a solution in the final joint space by integrating the calculated speed (speed vector $\dot{q}$ of a joint) of each joint in the joint space.

Next, the controller 540A transmits the desired rotational angle q of each of joints calculated by the redundancy utilization unit 546A to the servo controller 550A (Operation 660).

Subsequently, the servo controller 550A calculates a joint torque τ for tracking the desired rotational angle q of each of joints transmitted from the redundancy utilization unit 546A within the controller 540A and generates a torque control signal corresponding to the calculated joint torque τ (Operation 670).

Next, the servo controller 550A transmits the generated torque control signal to the driving unit 560A that rotationally drives each of joints that constitute the mounting arm 504L, the guide tube 512, and the plurality of tools 514a, 514b, and 514c (Operation 680).

Through this procedure, various individual objectives (to enlarge a workspace of the tool, to minimize rigidity required for each joint of the tool, to minimize a possibility of collision between the tool and a peripheral obstacle, to minimize a degree of freedom required for the tool, and to perform a complex task) are achieved using redundancy of the humanoid robot 500A, and simultaneously, operations of elements (a mounting arm, a guide tube, and a plurality of tools) of the humanoid robot 500A can be controlled in an integrated manner.

The method of FIG. 15 may be used in more general purpose systems and/or for methods of controlling such systems. For example, the method may be used in patrol robots and/or for controlling such robots so as to allow safe startup, operation, and/or shutdown of the robots.

Figure 16:
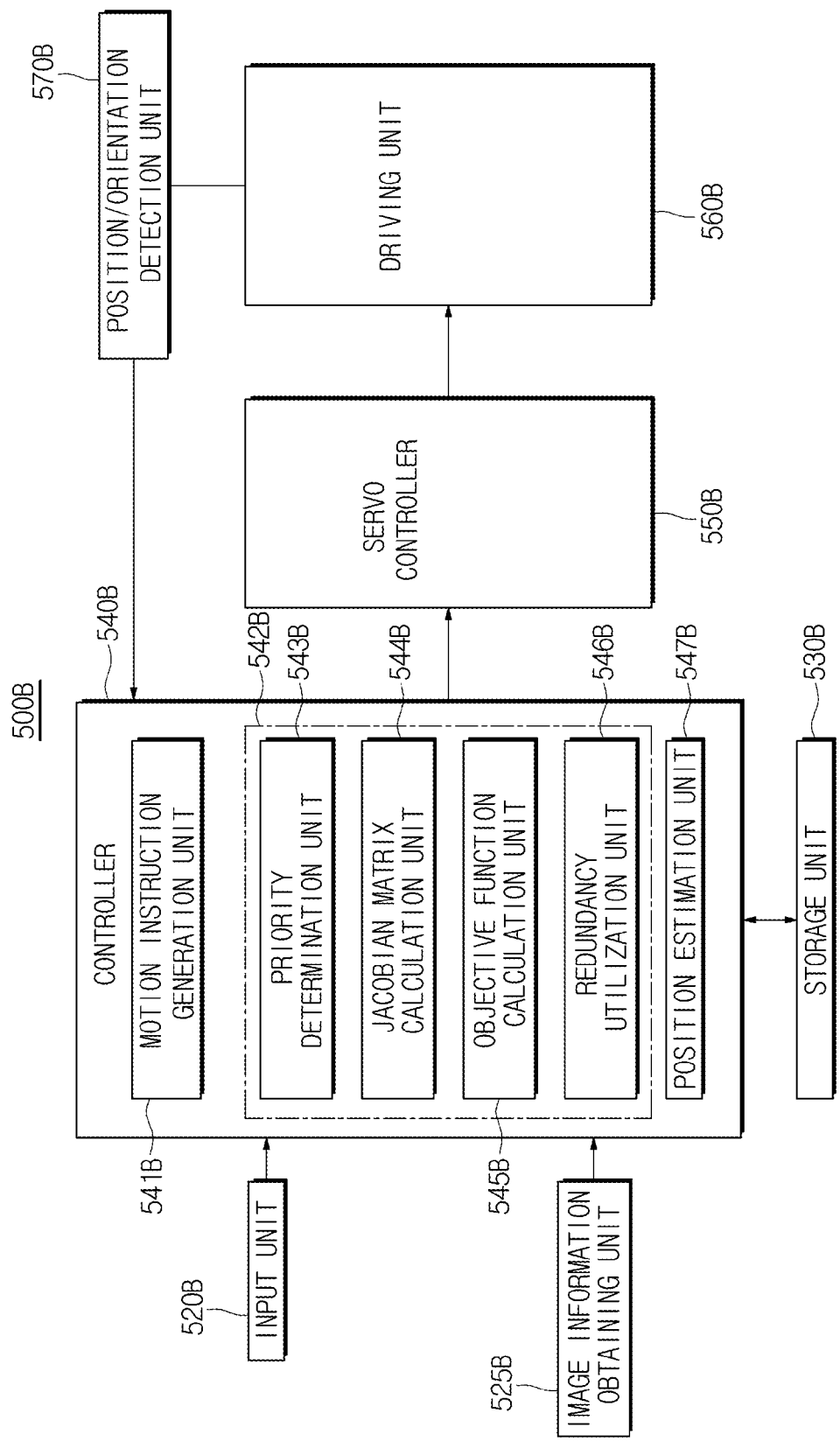
FIG. 16 is a control block diagram of a humanoid robot in accordance with some example embodiments.

FIG. 16 is a control block diagram of a humanoid robot in accordance with some example embodiments.

A humanoid robot 500B illustrated in FIG. 16 is different from the humanoid robot 500A illustrated in FIG. 14 in that a priority determination unit 543B is added to a redundancy inverse kinematics interpretation unit 542B of a controller 540B in comparison with the humanoid robot 500A of FIG. 14.

In some example embodiments, description of elements that use the same reference names and the same reference numerals as those of FIG. 14 will be omitted. (however, A and B marked after reference numerals are used to distinguish some example embodiments from each other.) A configuration of the priority determination unit 543B added to FIG. 16 and configurations of a storage unit 530B and the redundancy inverse kinematics interpretation unit 542B within the controller 540B, functions of which vary due to the priority determination unit 543B will now be described.

The storage unit 530B of FIG. 16 is a memory in which information and an algorithm required to calculate a solution in the joint space, i.e., a desired rotational angle of each of joints that constitute a mounting arm 504L, a guide tube 512, and a plurality of tools 514a, 514b, and 514c using redundancy of the humanoid robot 500B are stored. Priorities that are set to a task variable p, i.e., position/orientation information of the plurality of tools 514a, 514b, and 514c (for example, a higher priority is set to position/orientation information of the first tool 514a among the position/orientation information of the plurality of tools 514a, 514b, and 514c or a higher priority is set to position information $x_1$, $y_1$, and $z_1$ of the distal end of the first tool 514a between the position information $x_1$, $y_1$, and $z_1$ and orientation information $α_1$, $β_1$, and $γ_1$ of the distal end of the first tool 514a), an algorithm required to calculate a Jacobian matrix, information regarding a kinematics structure of the humanoid robot 500B, a plurality of individual objective functions for achieving a plurality of individual objectives required to calculate an objective function, and weights multiplied with individual objective functions depending on the type of the surgical task are stored in the storage unit 530B.

Also, the storage unit 530B may store the result of recognizing a position of the humanoid robot 500B and a map of the movement space that is drawn using an SLAM algorithm.

As illustrated in FIG. 16, the redundancy inverse kinematics interpretation unit 542B within the controller 540B that is an element for generating a control signal (desired rotational angle of each of a plurality of joints that constitute each element) for controlling operations in an integrated manner of elements (mounting arm, guide tube, and a plurality of tools) of the humanoid robot 500B using redundancy of the humanoid robot 500B includes the priority determination unit 543B, a Jacobian matrix calculation unit 544B, an objective function calculation unit 545B, and a redundancy utilization unit 546B.

Before describing the elements of the redundancy inverse kinematics interpretation unit 542B in detail, first, inverse kinematics interpretation when a priority is set to the task variable p in the humanoid robot 500B having redundancy will now be described.

When the system has redundancy, an inverse kinematics solution is calculated using a pseudo-inverse matrix $J^{\#}(q)$ of a Jacobian matrix $J(q)$, as described above.

In some example embodiments, when a priority is set to the task variable p, for example, when the task variable p is divided into $p_1$ and $p_2$ according to priorities and a higher priority is set to $p_1$, an equation for calculating a speed (speed vector $\dot{q}$ of a joint) of each joint in the joint space using the pseudo-inverse matrix of the Jacobian matrix may be represented as the following Equation 7, and $\hat{J}_2$ shown in Equation 7 may be defined as the following Equation 8.

$$\dot{q} = J_1^{\#}\dot{p}_1 + \hat{J}_2^{\#}(\dot{p}_2 - J_2 J_1^{\#}\dot{p}_1) + (I_n - J_1^{\#}J_1)(I_n - \hat{J}_2^{\#}\hat{J}_2)r \quad \text{[Equation 7]}$$

$$\hat{J}_2 = J_2(I_n - J_1^{\#}J_1) \quad \text{[Equation 8]}$$

In some example embodiments, $p_1$ and $p_2$ are subvectors that are obtained by classifying the task variable p according to priorities, $J_1$ and $J_2$ are Jacobian matrices corresponding to $p_1$ and $p_2$, $I_n$ is an n×n unit matrix (identity matrix), and r is an arbitrary vector.

In description of a method of assigning a priority to the task variable p, for example, a higher priority may be set to position and orientation information of the first tool 514a (when priorities between position/orientation information of different tools are different from each other) among the position and orientation information of the plurality of tools 514a, 514b, and 514c, or a higher priority may be set to position information $x_1$, $y_1$, and $z_1$ of the distal end of the first tool 514a between the position information $x_1$, $y_1$, and $z_1$ and orientation information $\alpha_1$, $\beta_1$, and $\gamma_1$ of the distal end of the first tool 514a (when priorities of position information and orientation information of one tool are different from each other).

Even when the task variable p is classified according to priorities, an arbitrary vector r(q) is defined and individual objective functions $w_1$ to $w_n$ and an objective function w of the whole system are defined so as to utilize redundancy, as shown in Equation 6 and as described above with reference to FIGS. 5 through 9, and thus, detailed description thereof will be omitted.

Referring back to FIG. 16, elements of the redundancy inverse kinematics interpretation unit 542B will be described in detail.

The priority determination unit 543B classifies position and orientation information x, y, z, $\alpha$, $\beta$, and $\gamma$ of a distal end (each distal end of a plurality of tools) of the humanoid robot 500B generated by a motion instruction generation unit 541B according to desired priorities (that may or may not be predetermined). In some example embodiments, it is premised that the position and orientation information of the distal end of the humanoid robot 500B, i.e., the task variable p is classified into $p_1$ and $p_2$ according to priorities, wherein a priority set to $p_1$ is higher than a priority set to $p_2$. For example, when a higher priority is set to position and orientation information of the first tool 514a among the position and orientation information of the plurality of tools 514a, 514b, and 514c (when priorities between position/orientation information of different tools are different from each other), the priority determination unit 543B determines the position and orientation information of the first tool 514a as $p_1$ and determines the orientation information of the second and third tools 514b and 514c as $p_2$. Also, for example, when a higher priority is set to position information $x_1$, $y_1$, and $z_1$ of the distal end of the first tool 514a between the position information $x_1$, $y_1$, and $z_1$ and orientation information $\alpha_1$, $\beta_1$, and $\gamma_1$ of the distal end of the first tool 514a (when priorities of position information and orientation information of one tool are different from each other), the priority determination unit 543B determines the position information $x_1$, $y_1$, and $z_1$ of the distal end of the first tool 514a as $p_1$ and determines the orientation information $\alpha_1$, $\beta_1$, and $\gamma_1$ of the distal end of the first tool 514a as $p_2$.

The Jacobian matrix calculation unit 544B calculates a Jacobian matrix $J_1(q)$ corresponding to $p_1$ having a relatively high priority and a Jacobian matrix $J_2(q)$ corresponding to $p_2$ having a relatively low priority of the task variable p by inputting pieces of information (for example, information regarding lengths of links that connect between a joint and a joint) regarding a kinematics structure of the humanoid robot 500B to an algorithm for calculating a Jacobian matrix.

The objective function calculation unit 545B calculates an objective function w shown in Equation 6, i.e., $$r = -k\frac{\partial w}{\partial q},$$

which represents an arbitrary vector r(q) shown in Equation 7, i.e., $\dot{q} = J_1^{\#}\dot{p}_1 + \hat{J}_2^{\#}(\dot{p}_2 - J_2 J_1^{\#}\dot{p}_1) + (I_n - J_1^{\#}J_1)(I_n - \hat{J}_2^{\#}\hat{J}_2)r$, which calculates a speed (speed vector $\dot{q}$ of a joint) of each joint in the joint space using a pseudo-inverse matrix $J_1^{\#}(q)$ of the Jacobian matrix $J_1(q)$ corresponding to $p_1$ having a relatively high priority of the task variable p and a pseudo-inverse matrix $J_2^{\#}(q)$ of the Jacobian matrix $J_2(q)$ corresponding to $p_2$ having a relatively low priority of the task variable p in the humanoid robot 500B having redundancy. The objective function w (objective function of the whole system) may be represented as a weighted sum of a plurality of individual objective functions $w_1$ to $w_n$ ($w = aw_1 + bw_2 + cw_3 + \ldots$). Examples of the individual objective functions may include a reciprocal number of a distance between each of the tools 514a, 514b, and 514c and a joint limit, a joint torque square sum that constitutes the plurality of tools 514a, 514b, and 514c, and a reciprocal number of a distance between each of the tools 514a, 514b, and 514c and a peripheral obstacle. In some example embodiments, the objective function w of the whole system varies depending on a flow of time. That is, the weights a, b, c, and . . . multiplied with the individual objective functions $w_1$ to $w_n$ vary depending on the type of the task performed by the humanoid robot 500B. The objective function calculation unit 545B determines the type of the task performed by the humanoid robot 500B, determines the weights a, b, c, and . . . multiplied with the individual objective functions $w_1$ to $w_n$ based on the result of determination, and then calculates the objective function w of the whole system by multiplying each of the individual objective functions by each determined weight.

The redundancy utilization unit 546B calculates a solution in the joint space in which the objective function w of the whole system is minimized, i.e., a desired rotational angle q of each of joints that constitute the mounting arm 504L, the guide tube 512, and the plurality of tools 514a, 514b, and 514c. The redundancy utilization unit 546B calculates a speed (speed vector $\dot{q}$ of a joint) of each joint in the joint space in which the objective function w is minimized, by substituting the objective function w calculated by the objective function calculation unit 545B with the above Equation 6 and then by substituting Equation 6 with which the objective function w is substituted, with the above Equation 7. The redundancy utilization unit 546B calculates the desired rotational angle q of each of joints that constitute the mounting arm 504L, the guide tube 512, and the plurality of tools 514a, 514b, and 514c that is the solution in the final joint space by integrating the calculated speed (speed vector $\dot{q}$ of a joint) of each joint in the joint space.

FIG. 17 is a flowchart illustrating a method of controlling a humanoid robot in accordance with some example embodiments.

As an initial condition for describing an operation of some example embodiments, it is premised that that the humanoid robot 500B, in particular, the left arm of the humanoid robot 500B illustrated in FIG. 13 has redundancy and each of the mounting arm 504L, the guide tube 512, and three tools 514a, 514b, and 514c includes a plurality of links and a plurality of joints. Also, it is premised that the mounting arm 504L and the guide tube 512 operate while interacting with each other and the guide tube 512 and each of the tools 514a, 514b, and 514c operate while interacting with each other. Also, it is premised that priorities set to a task variable p, i.e., position/orientation information of the plurality of tools 514a, 514b, and 514c, an algorithm required to calculate a Jacobian matrix, information regarding a kinematics structure of the humanoid robot 500B, a plurality of individual objective functions for achieving a plurality of individual objectives required to calculate an objective function, and weights multiplied with individual objective functions depending on the type of the task have been already stored in the storage unit 530B.

If a task instruction (for example, a cleaning instruction) of the humanoid robot 500B is input by the user through an input unit 520B, a task of the humanoid robot 500B starts.

First, if the task of the humanoid robot 500B starts, the controller 540B periodically receives position and orientation information of each distal end of the plurality of tools 514a, 514b, and 514c in the 3D space from a position/orientation detection unit 570B and performs the task (Operation 710).

Next, the motion instruction generation unit 541B within the controller 540B generates motion instructions x, y, z, $\alpha$, $\beta$, and $\gamma$ in the task space of the plurality of tools 514a, 514b, and 514c based on a user instruction signal transmitted from the input unit 520B, an image signal of the periphery of the movement space transmitted from an image information obtaining unit 525B, and position and orientation information of distal ends of the plurality of tools 514a, 514b, and 514c in the 3D space transmitted from the position/orientation detection unit 570B (Operation 720). In some example embodiments, the motion instructions x, y, z, $\alpha$, $\beta$, and $\gamma$ in the task space generated by the motion instruction generation unit 541B are a task variable p.

Subsequently, the priority determination unit 543B within the redundancy inverse kinematics interpretation unit 542B of the controller 540B classifies position and orientation information x, y, z, $\alpha$, $\beta$, and $\gamma$ of a distal end (each distal end of a plurality of tools) of the humanoid robot 500B generated by the motion instruction generation unit 541B according to desired priorities (that may or may not be predetermined) (Operation 730). When it is premised that the task variable p is classified into $p_1$ and $p_2$ according to priorities, wherein a priority set to $p_1$ is higher than a priority set to $p_2$, for example, when a higher priority is set to position and orientation information of the first tool 514a among the position and orientation information of the plurality of tools 514a, 514b, and 514c, the priority determination unit 543B determines the position and orientation information of the first tool 514a as $p_1$ and determines the orientation information of the second and third tools 514b and 514c as $p_2$.

Subsequently, the Jacobian matrix calculation unit 544B within the redundancy inverse kinematics interpretation unit 542B of the controller 540B calculates a Jacobian matrix $J_1(q)$ corresponding to $p_1$ having a relatively high priority and a Jacobian matrix $J_2(q)$ corresponding to $p_2$ having a relatively low priority of the task variable p using an algorithm for calculating a Jacobian matrix and pieces of information (for example, information regarding lengths of links that connect between a joint and a joint) regarding a kinematics structure of the humanoid robot 500B that have been already stored in the storage unit 530B (Operation 740).

Next, the objective function calculation unit 545B within the redundancy inverse kinematics interpretation unit 542B of the controller 540B determines the type of the task performed by the humanoid robot 500B, determines weights a, b, c, and . . . based on the result of determination, and then calculates an objective function w of the whole system by multiplying each of individual objective functions by each determined weight (Operation 750).

Next, the redundancy utilization unit 546B within the redundancy inverse kinematics interpretation unit 542B of the controller 540B calculates a desired rotational angle q of each of joints that constitute the mounting arm 504L, the guide tube 512, and the plurality of tools 514a, 514b, and 514c using redundancy of the humanoid robot 500B (Operation 760). In some example embodiments, the redundancy utilization unit 546B calculates a speed (speed vector $\dot{q}$ of a joint) of each joint in the joint space in which the objective function w of the whole system calculated by the objective function calculation unit 545B is minimized, and calculates the desired rotational angle q of each of joints that constitute the mounting arm 504L, the guide tube 512, and the plurality of tools 514a, 514b, and 514c that is a solution in the final joint space by integrating the calculated speed (speed vector $\dot{q}$ of a joint) of each joint in the joint space.

Subsequently, the controller 540B transmits the desired rotational angle q of each of joints calculated by the redundancy utilization unit 546B to a servo controller 550B (Operation 770).

Next, the servo controller 550B calculates a joint torque $\tau$ for tracking the desired rotational angle q of each of joints transmitted from the redundancy utilization unit 546B within the controller 540B and generates a torque control signal corresponding to the calculated joint torque τ (Operation 780).

Subsequently, the servo controller 550B transmits the generated torque control signal to a driving unit 560B that rotationally drives each of joints that constitute the mounting arm 504L, the guide tube 512, and the plurality of tools 514a, 514b, and 514c (Operation 790).

As shown in FIG. 16, slave robot 500B also may include position estimation unit 547B.

Through this procedure, various individual objectives (to enlarge a workspace of the tool, to minimize rigidity required for each joint of the tool, to minimize a possibility of collision between the tool and a peripheral obstacle, to minimize a degree of freedom required for the tool and to perform a complex task) are achieved using redundancy of the humanoid robot 500B, and simultaneously, operations of elements (a mounting arm, a guide tube, and a plurality of tools) of the humanoid robot 500B can be controlled in an integrated manner.

The method of FIG. 17 may be used in more general purpose systems and/or for methods of controlling such systems. For example, the method may be used in military robots and/or for controlling such robots so as to allow safe deployment, operation, and/or retrieval of the robots.

In the above-described example embodiments, a surgical robot or a humanoid robot has been described as a robot having a plurality of tools. However, some example embodiments may also be applied to various robot systems in which a plurality of tools are extended from a guide tube.

As described above, in a robot and a method of controlling the same according to the some example embodiments, a robot includes a mounting arm, a guide tube mounted on the mounting arm, and a plurality of tools having end effectors and extended from the guide tube, controls the mounting arm, the guide tube, and the plurality of tools to operate while interacting with each other, and utilizes redundancy generated due to a degree of freedom of a proximal end, i.e., the mounting arm and the guide tube, so that a workspace of the plurality of tools can be extended and a task that cannot be carried out by a conventional tool controlling method can be performed.

In a robot and a method of controlling the same according to some example embodiments, a robot includes a mounting arm, a guide tube mounted on the mounting arm, and a plurality of tools having end effectors and extended from the guide tube, controls the mounting arm, the guide tube, and the plurality of tools to operate while interacting with each other, and utilizes redundancy generated due to a degree of freedom of a proximal end, i.e., the mounting arm and the guide tube, so that rigidity required for joints of the tools can be minimized and a possibility of collision between the tools and a peripheral obstacle can be minimized.

In a robot and a method of controlling the same according to some example embodiments, a robot includes a mounting arm, a guide tube mounted on the mounting arm, and a plurality of tools having end effectors and extended from the guide tube, controls the mounting arm, the guide tube, and the plurality of tools to operate while interacting with each other, and utilizes redundancy generated due to a degree of freedom of a proximal end, i.e., the mounting arm and the guide tube, so that a degree of freedom required for the tools can be minimized and a complex task that cannot be performed by a conventional tool controlling method can be performed.

The algorithms discussed in this application (e.g., required to calculate a solution in the joint space, required to calculate a Jacobian matrix, required to control operation of the slave robot, SLAM algorithm) may be used in more general purpose robots and/or methods of controlling robots. For example, the algorithms may be used in robots for handling hazardous materials and/or for controlling such robots so as to allow safe movement, packaging, and/or shipment of hazardous materials.

The methods described above may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' means software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiment, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to surgical robot systems, those skilled in the art will appreciate that some example embodiments may be applied to other types of systems, such as systems not used in the medical field (e.g., aerospace teleoperation systems, robots for handling hazardous materials, patrol robots, military robots), humanoid robots, or more general purpose control systems. Those skilled in the art will appreciate that the humanoid robots described in this application have a myriad of practical uses.

While example embodiments have been particularly shown and described, it will be understood by those of ordinary skill in the art that various changes in form and details may be made therein without departing from the spirit and scope of the present invention as defined by the following claims.

What is claimed is:

1. A robot, comprising:
a multi-tool module having redundancy, the multi-tool module including,
  a guide tube including a plurality of first links and a plurality of first joints; and
  a plurality of tools configured to operate while interacting with the guide tube and extend from the guide tube; and
a controller configured to execute computer readable instruction to generate a control signal regarding motion of the multi-tool module in a joint space based on motion instruction information regarding distal ends of the plurality of tools in a task space, wherein
  the redundancy indicates that a number of degrees of freedom of the multi-tool module in the joint space is greater than a number of degrees of freedom in the task space,
  the control signal is generated using the redundancy,
  the controller is further configured to calculate an objective function of the robot when the control signal is generated, the objective function is a base in quantitative evaluation of at least one of optimization and an achievement of an objective, and the objective function represents a weighted sum of a plurality of individual objective functions, the plurality of individual objective functions includes (i) a joint torque square sum, (ii) a reciprocal number of a distance between each of the plurality of tools and a joint limit, and (iii) a reciprocal number of a distance between each of the plurality of tools and a singular pose.

2. The robot of claim 1, wherein
each of the plurality of tools includes a plurality of second links and a plurality of second joints, and
the distal ends of each of the plurality of tools includes end effectors.

3. The robot of claim 1, wherein the controller is further configured to execute the computer readable instructions to,
calculate a Jacobian matrix corresponding to the motion instruction information, and
generate the control signal based on the motion instruction information and the calculated Jacobian matrix using the redundancy.

4. The robot of claim 1, wherein the plurality of individual objective functions further includes a reciprocal number of a distance between each of the plurality of tools and a peripheral obstacle.

5. The robot of claim 1, wherein the controller is further configured to execute the computer readable instructions to,
generate the control signal in which the calculated objective function of the robot is optimized or sub-optimized by maximizing or minimizing a value of the objective function.

6. The robot of claim 1, further comprising:
a memory configured to,
  store an algorithm required to calculate a Jacobian matrix, and
  store (i) information regarding a kinematics structure of the robot, (ii) the plurality of individual objective functions for achieving a plurality of individual objectives required to calculate the objective function, and (iii) weights multiplied with the plurality of individual objective functions depending on a type of a task performed by the robot.

7. The robot of claim 1, wherein when priorities are set to the motion instruction information regarding the distal ends of the plurality of tools in the task space, the controller is further configured to execute the computer readable instructions to,
calculate Jacobian matrices corresponding to the motion instruction information having a relatively high priority in the task space and the motion instruction information having a relatively low priority in the task space, and
generate the control signal based on the motion instruction information in the task space to which the priorities are set and the calculated Jacobian matrices using the redundancy.

8. The robot of claim 7, wherein the controller is further configured to execute the computer readable instructions to,
generate the control signal in which the calculated objective function of the robot is optimized or sub-optimized by maximizing or minimizing a value of the objective function.

9. The robot of claim 7, further comprising:
a memory configured to,
  store the priorities set to the motion instruction information regarding the distal ends of the plurality of tools in the task space, an algorithm required to calculate the Jacobian matrices and information regarding a kinematics structure of the robot, the plurality of individual objective functions for achieving a plurality of individual objectives required to calculate the objective function, and weights multiplied with the plurality of individual objective functions depending on a type of a task performed by the robot.

10. A method of controlling a robot including a multi-tool module having redundancy, the multi-tool module including a guide tube and a plurality of tools, the guide tube including a plurality of first links and a plurality of first joints, and the plurality of tools configured to operate while interacting with the guide tube and extend from the guide tube, the method comprising:

generating motion instruction information regarding distal ends of the plurality of tools in a task space;

generating a control signal regarding motion of the multi-tool module in a joint space based on the generated motion instruction information in the task space; and controlling the robot according to the control signal; wherein the redundancy indicates that a number of degrees of freedom of the multi-tool module in the joint space is greater than a number of degrees of freedom of the task space, the control signal is generated using the redundancy, and the generating of the control signal includes calculating an objective function of the robot, the objective function is a base in quantitative evaluation of at least one of optimization and an achievement of an objective, and the objective function represents a weighted sum of a plurality of individual objective functions, the plurality of individual objective functions includes (i) a joint torque square sum, (ii) a reciprocal number of a distance between each of the plurality of tools and a joint limit, and (iii) a reciprocal number of a distance between each of the plurality of tools and a singular pose.

11. The method of claim 10, wherein each of the plurality of tools includes a plurality of second links and a plurality of second joints, and the distal ends of each of the plurality of tools includes end effectors.

12. The method of claim 10, wherein the generating of the control signal further includes, calculating a Jacobian matrix corresponding to the motion instruction information; and generating the control signal based on the motion instruction information and the calculated Jacobian matrix using the redundancy.

13. The method of claim 12, wherein the generating of the control signal further includes, generating the control signal in which the calculated objective function of the robot is optimized or sub-optimized by maximizing or minimizing a value of the objective function.

* * * * *